United States Patent
Coats et al.

(10) Patent No.: US 9,926,295 B2
(45) Date of Patent: *Mar. 27, 2018

(54) POTENT AND SELECTIVE INHIBITORS OF HEPATITIS C VIRUS

(71) Applicants: Cocrystal Pharma, Inc., Tucker, GA (US); Emory University, Atlanta, GA (US)

(72) Inventors: Steven J. Coats, Tucker, GA (US); Richard Anthony Whitaker, Tucker, GA (US); Tamara Rosario McBrayer, Tucker, GA (US); Junxing Shi, Tucker, GA (US); Franck Amblard, Atlanta, GA (US); Hongwang Zhang, Atlanta, GA (US); Longhu Zhou, Atlanta, GA (US); Raymond F. Schinazi, Atlanta, GA (US)

(73) Assignees: Cocrystal Pharma, Inc., Tucker, GA (US); Emory University, Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/303,277

(22) PCT Filed: Apr. 15, 2015

(86) PCT No.: PCT/US2015/025903
§ 371 (c)(1),
(2) Date: Oct. 11, 2016

(87) PCT Pub. No.: WO2015/160907
PCT Pub. Date: Oct. 22, 2015

(65) Prior Publication Data
US 2017/0029407 A1  Feb. 2, 2017

Related U.S. Application Data

(60) Provisional application No. 61/980,016, filed on Apr. 15, 2014.

(51) Int. Cl.
| | |
|---|---|
| *C07D 401/14* | (2006.01) |
| *A61K 31/4178* | (2006.01) |
| *A61K 45/06* | (2006.01) |
| *C07D 403/14* | (2006.01) |

(52) U.S. Cl.
CPC ........ *C07D 401/14* (2013.01); *A61K 31/4178* (2013.01); *A61K 45/06* (2013.01); *C07D 403/14* (2013.01)

(58) Field of Classification Search
None
See application file for complete search history.

(56) References Cited

U.S. PATENT DOCUMENTS 8,859,595 B2 * 10/2014 Coats ................. A61K 31/4178
514/359

FOREIGN PATENT DOCUMENTS

| WO | 2009102325 A1 | 8/2009 | |
|---|---|---|---|
| WO | 2011075439 A1 | 6/2011 | |
| WO | WO 2012/048421 A1 * | 4/2012 | ........... C07D 403/14 |

OTHER PUBLICATIONS

International Search Report dated Nov. 3, 2016 for PCT Application No. PCT/US2015/025903.

* cited by examiner

*Primary Examiner* — Brian J Davis
(74) *Attorney, Agent, or Firm* — David Bradin; Andrews Kurth Kenyon LLP

(57) ABSTRACT

The present invention is directed to compounds, compositions and methods for treating or preventing hepatitis C virus (HCV) infection in human subjects or other animal hosts. The compounds are as also pharmaceutically acceptable, salts, prodrugs, and other derivatives thereof as pharmaceutical compositions and methods for treatment or prevention of HCV infection.

13 Claims, 2 Drawing Sheets

POTENT AND SELECTIVE INHIBITORS OF HEPATITIS C VIRUS

CROSS-REFERENCE TO RELATED APPLICATIONS

This application claims priority under 35 U.S.C. 371 to PCT/US2015/025903, filed on Apr. 15, 2015, which in turn claims priority to U.S. Provisional Application Ser. No. 61/980,016, filed on Apr. 15, 2014. The contents of each of these applications is incorporated by reference in their entirety for all purposes.

FIELD OF THE INVENTION

The present invention is directed to compounds, methods and compositions for treating or preventing hepatitis C virus (HCV) infections. More specifically, the invention describes specifically substituted aromatic compounds, pharmaceutically acceptable salts, or other derivatives thereof, and the use thereof in the treatment of HCV infection. Most of these compounds target the HCV NS5A phosphoprotein.

BACKGROUND OF THE INVENTION

Hepatitis C virus (HCV) has infected more than 180 million people worldwide. It is estimated that three to four million persons are newly infected each year, 70% of whom will develop chronic hepatitis. HCV is responsible for 50-76% of all liver cancer cases, and two thirds of all liver transplants in the developed world. Standard therapy [pegylated interferon alfa plus ribavirin (a nucleoside analog)] is only effective in 50-60% of patients and is associated with significant side-effects. Therefore, there is an urgent need for new HCV drugs.

Hepatitis C virus genome comprises a positive-strand RNA enclosed in a nucleocapsid and lipid envelope and consists of 9.6 kb ribonucleotides and has a single open reading frame (ORP) encoding which encodes a large polypeptide of about 3000 amino acids (Dymock et al. Antiviral Chemistry & Chemotherapy 2000, 11, 79). Following maturation, this polypeptide is cut into at least 10 proteins by cellular and viral proteases to produce the structural and non-structural (NS) proteins. In the case of HCV, the generation of mature non-structural proteins (NS2, NS3, NS4A, NS4B, NS5A, and NS5B) is effected by two viral proteases: 1) a metalloprotease that cleaves at the NS2-NS3 junction; and 2) a serine protease contained within the N-terminal region of NS3 (NS3 protease) which mediates all the subsequent cleavages downstream of NS3. The NS4A protein appears to serve multiple functions including the NS4A/NS3 complex formation, which appears to enhance the proteolytic efficiency of the NS3 protein. NS5B (also referred to herein as HCV polymerase), possesses polymerase activity and is involved in the synthesis of double-stranded RNA from the single-stranded viral RNA genome that serves as the template. NS5A is a nonstructural 56-58 kDa protein which modulates HCV replication as a component of replication complex. NS5A is highly phosphorylated by cellular protein kinases and the phosphorylation sites are conserved among HCV genotypes (Katze et al, 2001; Kim et al, 1999)

The discovery of novel antiviral strategies to selectively inhibit HCV replication has long been hindered by the lack of convenient cell culture models for the propagation of HCV ("Recent Advances in Nucleoside Monophosphate Prodrugs as Anti-hepatitis C Virus Agents" Bobeck, D. R.; Coats, S. J.; Schinazi, R. F. Antivir. Ther. 2010; Book Chapter: "Approaches for the Development of Antiviral Compounds: The Case of Hepatitis C Virus." Raymond F. Schinazi, Steven J. Coats, Leda C. Bassit, Johan Lennerstrand, James H. Nettles, and Selwyn J. Hurwitz in: Handbook of Experimental Pharmacology, vol. 189, 25-51: Antiviral Strategies; Edited by: Hans-Georg Kriusslich and Ralf Bartenschlager© Springer-Verlag Berlin Heidelberg 2009). This hurdle has been overcome first with the establishment of the HCV replicon system in 1999 (Bartenschlager, R., Nat. Rev. Drug Discov. 2002, 1, 911-916 and Bartenschlager, R., J. Hepatol. 2005, 43, 210-216) and, in 2005, with the development of robust HCV cell culture models (Wakita, T., et al., Nat. Med. 2005, 11, 791-6; Zhong, J., et al., Proc. Natl. Acad. Sci. U.S.A. 2005, 102, 9294-9; Lindenbach, B. D., et al., Science 2005, 309, 623-6).

It would be advantageous to provide new antiviral agents, compositions including these agents, and methods of treatment using these agents, particularly to treat HCV and drug-resistant HCV. The present invention provides such agents, compositions and methods.

SUMMARY OF THE INVENTION

The present invention provides compounds, methods and compositions for treating or preventing HCV infection in a host. The methods involve administering a therapeutically or prophylactically-effective amount of at least one compound as described herein to treat or prevent an infection by, or an amount sufficient to reduce the biological activity of HCV infection. The pharmaceutical compositions include one or more of the compounds described herein, in combination with a pharmaceutically acceptable carrier or excipient, for treating a host infected with HCV. These compounds can be used in combination with nucleoside and non-nucleoside inhibitors of HCV. The formulations can further include at least one other therapeutic agent. In addition, the present invention includes processes for preparing such compounds.

In one embodiment, the active compound is of Formula (I):

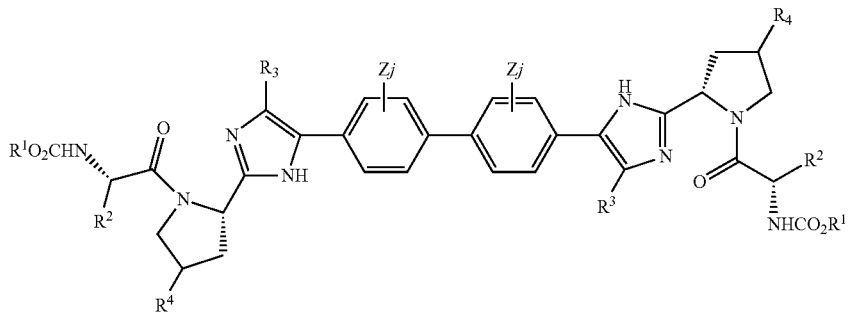

R[1] is, independently, H, $C_{1-6}$ alkyl, aryl-$C_{1-6}$-alkyl, $C_{1-6}$ alkyl-aryl, or aryl, R[2] is, independently, H, $C_{1-6}$ alkyl, aryl-$C_{1-6}$-alkyl, including $C_{3-6}$ branched alkyl, $C_{1-6}$ alkyl-aryl, aryl, $C_{1-6}$ alkyl-guanidine, $C_{1-6}$ alkylamino, $C_{1-6}$ alkyl-S—$C_{1-6}$ alkyl, $C_{1-6}$ alkylthiol, $C_{1-6}$ alkyl-hydroxy, $C_{1-6}$ alkyl-amide, $C_{1-6}$ alkyl-phenoxy, $C_{1-6}$ alkyl-carboxy heteroaryl, and heteroaryl-$C_{1-6}$ alkyl, wherein aryl rings can be substituted with from 1 to 3 substituents Z as defined herein, R[3] is, independently, H or Cl, with the proviso that at least one R[3] is Cl, R[4] is, independently, H or —S(O)$_x$—R[1], with the proviso that at least one R[4] is —S(O)$_x$—R[1].

Z is selected from the group consisting of $C_{1-8}$ alkyl (including cycloalkyl), lower alkenyl ($C_{2-6}$), lower alkynyl ($C_{2-6}$), heterocyclyl, aryl, heteroaryl, arylalkoxycarbonyl, carboxy, halo (e.g., F, Cl, Br, or I), haloalkyl, —OR', —NR'R", hydroxy, hydroxy-$C_{1-6}$ alkyl, alkoxyalkyl($C_{2-8}$), alkoxycarbonyl, —CF$_3$, —CN, —NO$_2$, —C$_2$R', —SR', —N$_3$, —C(=O)NR'R", —NR'C(=O)R", —C(=O)R', —C(=O)OR', —OC(=O)R', —OC(=O)NR'R", —NR'C(=O)OR", —SO$_2$R', —SO$_2$NR'R", —NR'SO$_2$R", N(R')$_2$, SR', OCOR', N(COR')R', N(COR')COR', and SCOR', Each R' and R" are, independently, H, a lower alkyl ($C_{1-6}$), lower haloalkyl ($C_{1-6}$), lower alkoxy ($C_{1-6}$), lower alkenyl ($C_{2-6}$), lower alkynyl ($C_{2-6}$), lower cycloalkyl ($C_{3-6}$), aryl, heteroaryl, heterocyclyl, alkylaryl, aryl-$C_{1-6}$-alkyl (such as benzyl); or if two R' reside on the same nitrogen atom they can come together to form an alkyl ring ($C_{3-6}$) containing none or one heteroatom independently selected from N, O, and S; wherein the R' groups can be substituted with one or more substituents as defined above, for example, hydroxyalkyl, aminoalkyl, and alkoxyalkyl, j is 0-4, and x is 0-2.

The compounds described herein can be in the form of the R- or S-configuration, or a mixture thereof, including a racemic or diastereomeric mixture thereof.

In one embodiment, one or both of the R[2] substituents are phenyl or phenyl substituted with one or more substituents Z as defined herein.

In one embodiment, one, two, or three of the R[1] substituents are —CH$_3$.

In one embodiment, each R[1] is —CH$_3$ and both of the R[2] substituents are phenyl or phenyl substituted with one or more substituents Z as defined herein.

A subset of the compounds of Formula (I) is provided below as Formula (IA):

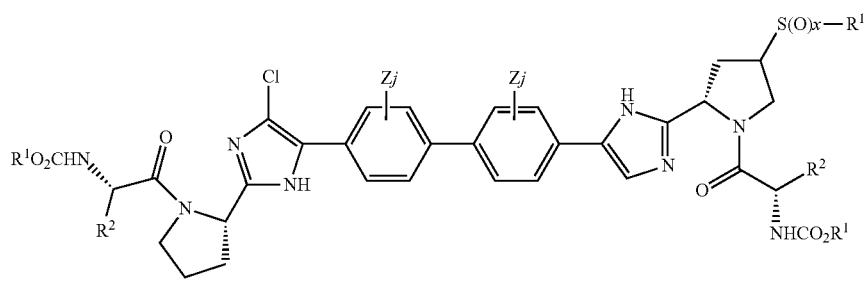

In which R[1], R[2], Z, R', R", j, and x are as defined with respect to Formula (I).

Representative compounds include the following:

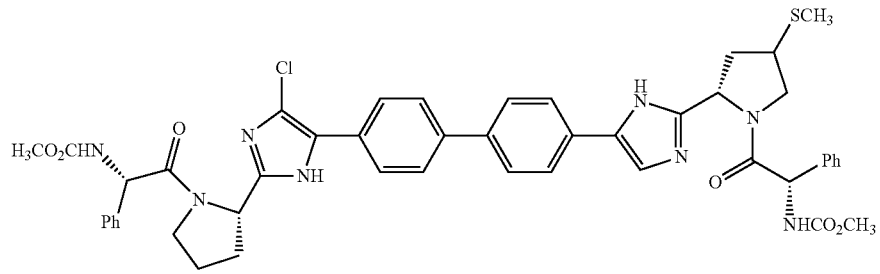

and all other diastereomers thereof, as well as —S(O)—CH$_3$ and —S(O)$_2$—CH$_3$ analogs thereof.

Further representative compounds have one of the following formulas:

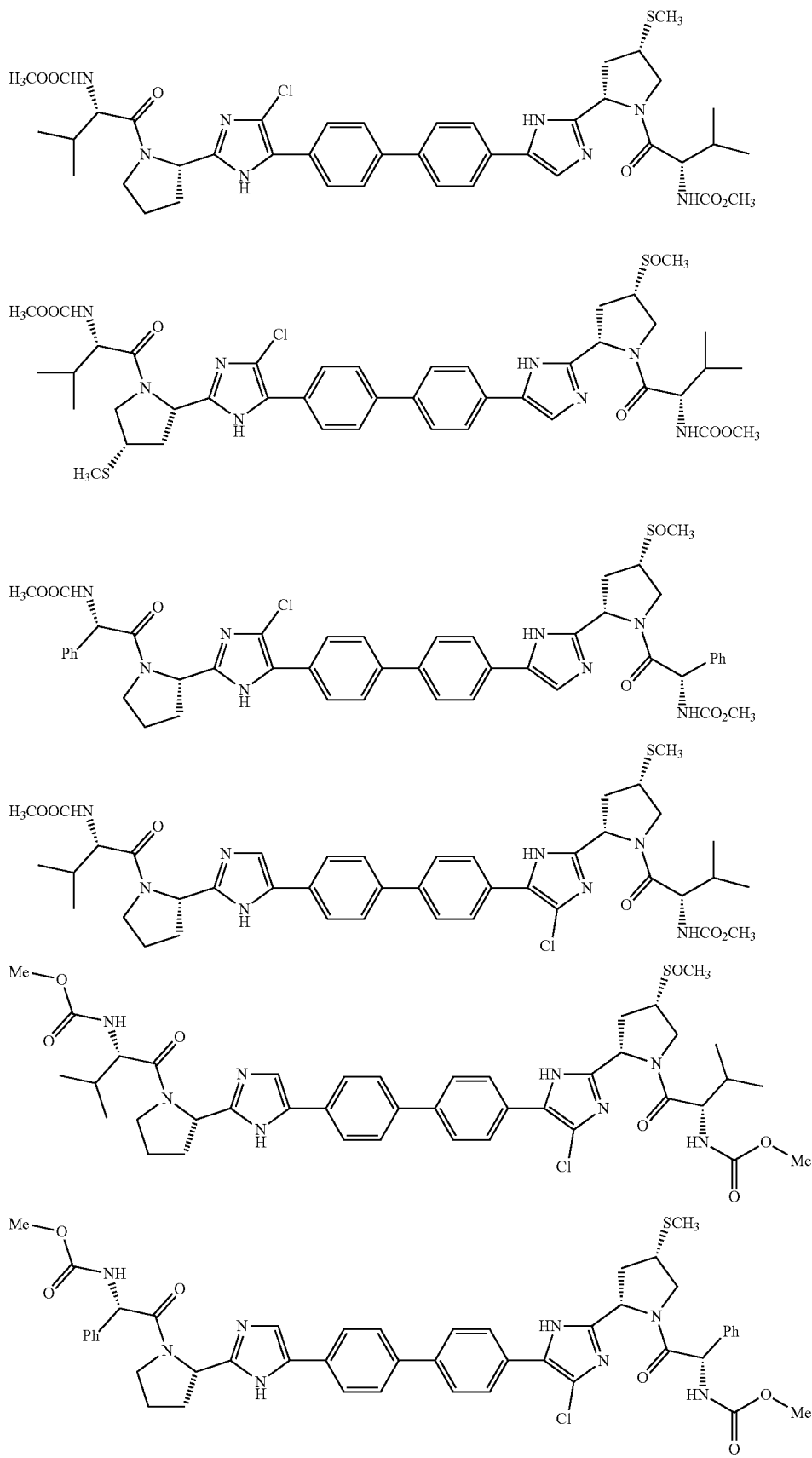

-continued

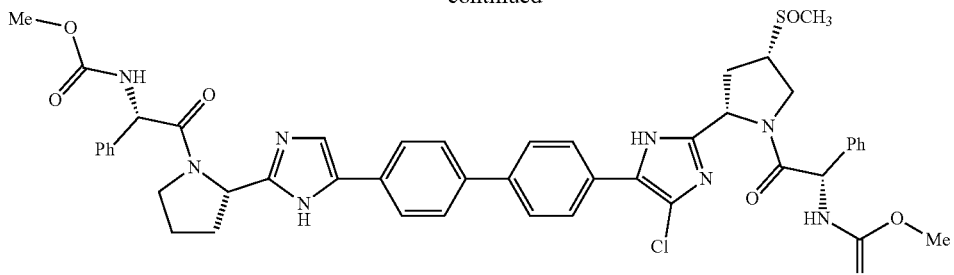

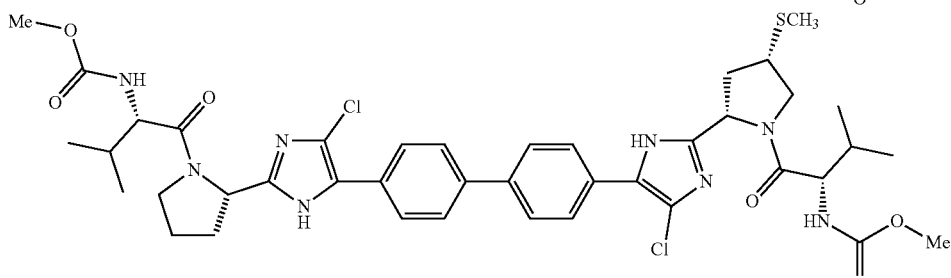

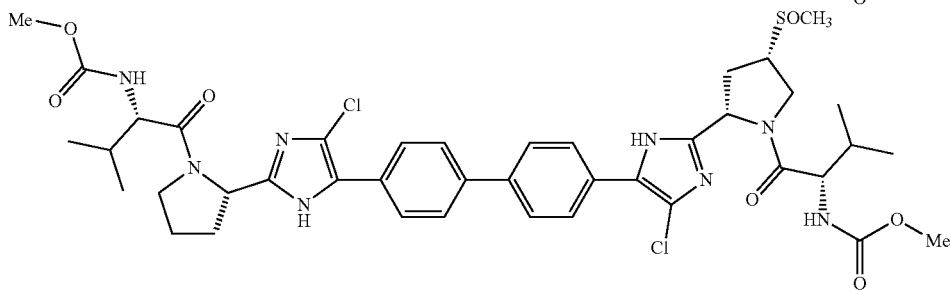

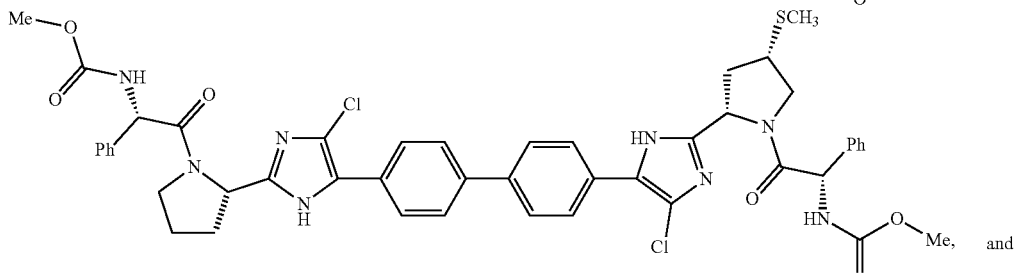

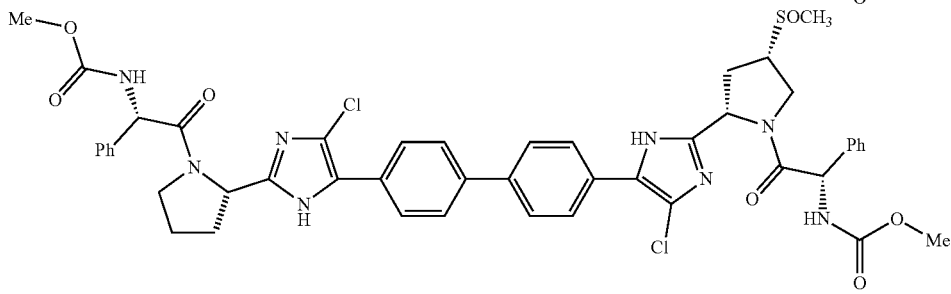 and and pharmaceutically-acceptable salts or prodrugs thereof.

The compounds can be used in combination therapy, for example, using conventional ribavirin/Pegasys therapy. Representative anti-HCV agents for use in combination therapy include, but are not limited to, a combination of Pegylated interferon (Pegasys) and ribavirin, polymerase inhibitors such as IDX-375 and IDX-184 (Idenix), PSI-7851 and PSI-7977 (Pharmasset) danoprevir (InterMune/Genentech), RG7128 (Pharmasset/Genentech), I ANA598 (Anadys Pharmaceuticals), TMN-191 (R7227), combinations of RG7128 and RG7227 (Genentech, Pharmasset and Intermune), ABT-072 (Abbott), VX-916, VX-759, VX-222, and VX-500 (Vertex), Filibuvir (PF-00868554) (Pfizer), GS 9190 (Gilead), alone or with boosters such as ritonavir, and serine protease inhibitors such as Boceprevir (SCH 503034) (Schering Plough), BILN-2061, Telaprevir (Vertex), ACH-1625 (Achillion), GS-9256 (Gilead), BI 201335 (Boehringer Ingelheim Pharma), Vaniprevir (MK-7009) (Merck), SCH900518 (Narlaprevir) (Schering/Merck), TMC435 (Medivir/Tibotec). Additional examples of serine protease inhibitors are provided, for example, in Reiser and Timm, "Serine protease inhibitors as anti-hepatitis C virus agents," Expert Review of Anti-infective Therapy, 7(5):537-547 (June 2009), the contents of which are hereby incorporated by reference.

The present invention will be better understood with reference to the following detailed description.

DETAILED DESCRIPTION

Figure 1:
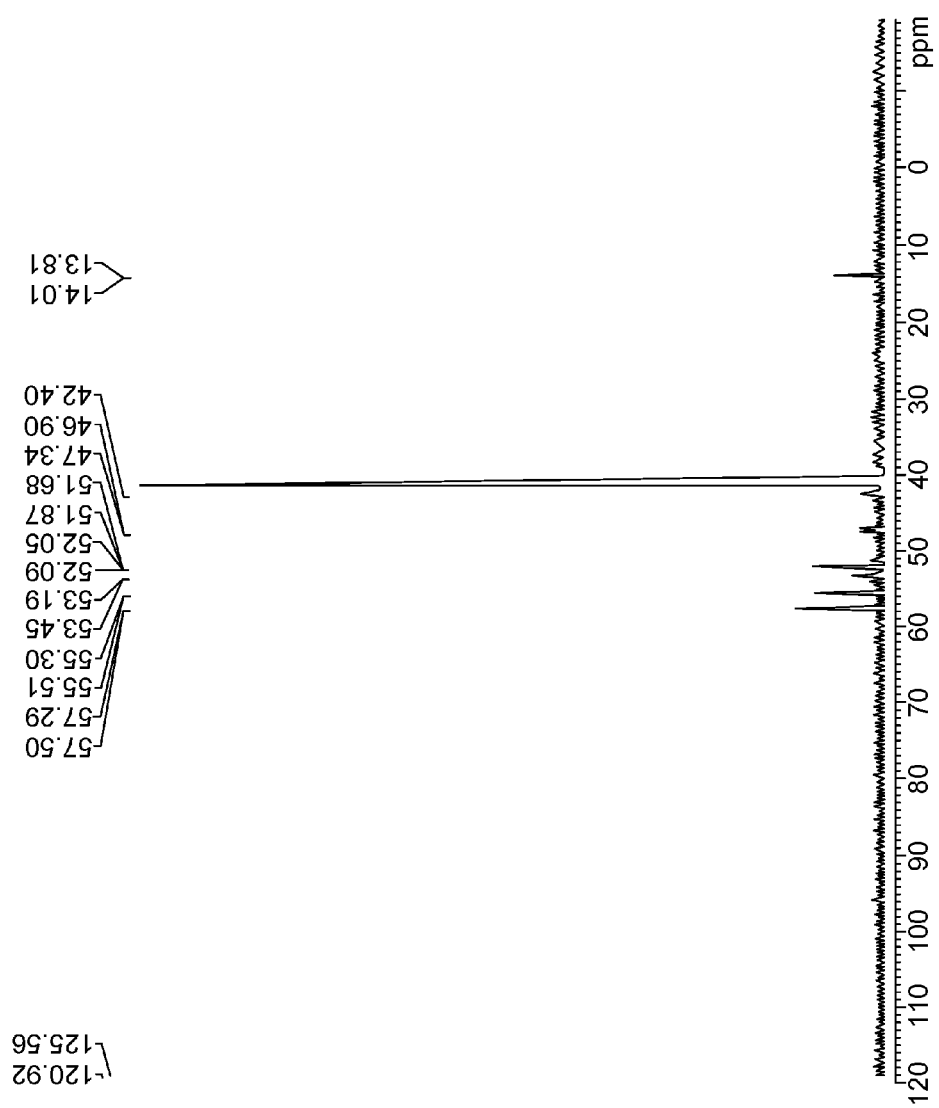
FIG. 1 is an $^{13}$C NMR spectrum of compound 30.

The compounds described herein show inhibitory activity against HCV in cell-based assays. Therefore, the compounds can be used to treat or prevent a HCV in a host, or reduce the biological activity of the virus. The host can be a mammal, and in particular, a human, infected with HCV. The methods involve administering an effective amount of one or more of the compounds described herein.

Pharmaceutical formulations including one or more compounds described herein, in combination with a pharmaceutically acceptable carrier or excipient, are also disclosed. In one embodiment, the formulations include at least one compound described herein and at least one further therapeutic agent.

The present invention will be better understood with reference to the following definitions:

I. Definitions

The term "independently" is used herein to indicate that the variable, which is independently applied, varies independently from application to application. Thus, in a compound such as R"XYR", wherein R" is "independently carbon or nitrogen," both R" can be carbon, both R" can be nitrogen, or one R" can be carbon and the other R" nitrogen.

As used herein, the term "enantiomerically pure" refers to a compound composition that comprises at least approximately 95%, and, preferably, approximately 97%, 98%, 99% or 100% of a single enantiomer of that compound.

As used herein, the term "substantially free of" or "substantially in the absence of" refers to a compound composition that includes at least 85 to 90% by weight, preferably 95% to 98% by weight, and, even more preferably, 99% to 100% by weight, of the designated enantiomer of that compound. In a preferred embodiment, the compounds described herein are substantially free of enantiomers.

Similarly, the term "isolated" refers to a compound composition that includes at least 85 to 90% by weight, preferably 95% to 98% by weight, and, even more preferably, 99% to 100% by weight, of the compound, the remainder comprising other chemical species or enantiomers.

The term "alkyl," as used herein, unless otherwise specified, refers to a saturated straight, branched, or cyclic, primary, secondary, or tertiary hydrocarbons, including both substituted and unsubstituted alkyl groups. The alkyl group can be optionally substituted with any moiety that does not otherwise interfere with the reaction or that provides an improvement in the process, including but not limited to but limited to halo, haloalkyl, hydroxyl, carboxyl, acyl, aryl, acyloxy, amino, amido, carboxyl derivatives, alkylamino, dialkylamino, arylamino, alkoxy, aryloxy, nitro, cyano, sulfonic acid, thiol, imine, sulfonyl, sulfanyl, sulfinyl, sulfamonyl, ester, carboxylic acid, amide, phosphonyl, phosphinyl, phosphoryl, phosphine, thioester, thioether, acid halide, anhydride, oxime, hydrozine, carbamate, phosphonic acid, phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference. Specifically included are $CF_3$ and $CH_2CF_3$.

In the text, whenever the term C(alkyl range) is used, the term independently includes each member of that class as if specifically and separately set out. The term "alkyl" includes $C_{1-22}$ alkyl moieties, and the term "lower alkyl" includes $C_{1-6}$ alkyl moieties. It is understood to those of ordinary skill in the art that the relevant alkyl radical is named by replacing the suffix "-ane" with the suffix "-yl".

As used herein, a "bridged alkyl" refers to a bicyclo- or tricyclo alkane, for example, a 2:1:1 bicyclohexane.

As used herein, a "spiro alkyl" refers to two rings that are attached at a single (quaternary) carbon atom.

The term "alkenyl" refers to an unsaturated, hydrocarbon radical, linear or branched, in so much as it contains one or more double bonds. The alkenyl group disclosed herein can be optionally substituted with any moiety that does not adversely affect the reaction process, including but not limited to but not limited to those described for substituents on alkyl moieties. Non-limiting examples of alkenyl groups include ethylene, methylethylene, isopropylidene, 1,2-ethane-diyl, 1,1-ethane-diyl, 1,3-propane-diyl, 1,2-propane-diyl, 1,3-butane-diyl, and 1,4-butane-diyl.

The term "alkynyl" refers to an unsaturated, acyclic hydrocarbon radical, linear or branched, in so much as it contains one or more triple bonds. The alkynyl group can be optionally substituted with any moiety that does not adversely affect the reaction process, including but not limited to those described above for alkyl moieties. Non-limiting examples of suitable alkynyl groups include ethynyl, propynyl, hydroxypropynyl, butyn-1-yl, butyn-2-yl, pentyn-1-yl, pentyn-2-yl, 4-methoxypentyn-2-yl, 3-methylbutyn-1-yl, hexyn-1-yl, hexyn-2-yl, and hexyn-3-yl, 3,3-dimethylbutyn-1-yl radicals.

The term "alkylamino" or "arylamino" refers to an amino group that has one or two alkyl or aryl substituents, respectively.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis, and are described, for example, in Greene et al., Protective Groups in Organic Synthesis, supra.

The term "aryl", alone or in combination, means a carbocyclic aromatic system containing one, two or three rings wherein such rings can be attached together in a pendent manner or can be fused. Non-limiting examples of aryl include phenyl, biphenyl, or naphthyl, or other aromatic groups that remain after the removal of a hydrogen from an aromatic ring. The term aryl includes both substituted and unsubstituted moieties. The aryl group can be optionally substituted with any moiety that does not adversely affect the process, including but not limited to but not limited to those described above for alkyl moieties. Non-limiting examples of substituted aryl include heteroarylamino, N-aryl-N-alkylamino, N-heteroarylamino-N-alkylamino, heteroaralkoxy, arylamino, aralkylamino, arylthio, monoarylamidosulfonyl, arylsulfonamido, diarylamidosulfonyl, monoaryl amidosulfonyl, arylsulfinyl, arylsulfonyl, heteroarylthio, heteroarylsulfinyl, heteroarylsulfonyl, aroyl, heteroaroyl, aralkanoyl, heteroaralkanoyl, hydroxyaralkyl, hydoxyheteroaralkyl, haloalkoxyalkyl, aryl, aralkyl, aryloxy, aralkoxy, aryloxyalkyl, saturated heterocyclyl, partially saturated heterocyclyl, heteroaryl, heteroaryloxy, heteroaryloxyalkyl, arylalkyl, heteroarylalkyl, arylalkenyl, and heteroarylalkenyl, carboaralkoxy.

The terms "alkaryl" or "alkylaryl" refer to an alkyl group with an aryl substituent. The terms "aralkyl" or "arylalkyl" refer to an aryl group with an alkyl substituent.

The term "halo," as used herein, includes chloro, bromo, iodo and fluoro.

The term "acyl" refers to a carboxylic acid ester in which the non-carbonyl moiety of the ester group is selected from straight, branched, or cyclic alkyl or lower alkyl, alkoxyalkyl including but not limited to methoxymethyl, aralkyl including but not limited to benzyl, aryloxyalkyl such as phenoxymethyl, aryl including but not limited to phenyl optionally substituted with halogen (F, Cl, Br, I), alkyl (including but not limited to $C_1$, $C_2$, $C_3$, and $C_4$) or alkoxy (including but not limited to $C_1$, $C_2$, $C_3$, and $C_4$), sulfonate esters such as alkyl or aralkyl sulphonyl including but not limited to methanesulfonyl, the mono, di or triphosphate ester, trityl or monomethoxytrityl, substituted benzyl, trialkylsilyl (e.g., dimethyl-t-butylsilyl) or diphenylmethylsilyl. Aryl groups in the esters optimally comprise a phenyl group. The term "lower acyl" refers to an acyl group in which the non-carbonyl moiety is lower alkyl.

The terms "alkoxy" and "alkoxyalkyl" embrace linear or branched oxy-containing radicals having alkyl moieties, such as methoxy radical. The term "alkoxyalkyl" also embraces alkyl radicals having one or more alkoxy radicals attached to the alkyl radical, that is, to form monoalkoxyalkyl and dialkoxyalkyl radicals. The "alkoxy" radicals can be further substituted with one or more halo atoms, such as fluoro, chloro or bromo, to provide "haloalkoxy" radicals. Examples of such radicals include fluoromethoxy, chloromethoxy, trifluoromethoxy, difluoromethoxy, trifluoroethoxy, fluoroethoxy, tetrafluoroethoxy, pentafluoroethoxy, and fluoropropoxy.

The term "alkylamino" denotes "monoalkylamino" and "dialkylamino" containing one or two alkyl radicals, respectively, attached to an amino radical. The terms arylamino denotes "monoarylamino" and "diarylamino" containing one or two aryl radicals, respectively, attached to an amino radical. The term "aralkylamino", embraces aralkyl radicals attached to an amino radical. The term aralkylamino denotes "monoaralkylamino" and "diaralkylamino" containing one or two aralkyl radicals, respectively, attached to an amino radical. The term aralkylamino further denotes "monoaralkyl monoalkylamino" containing one aralkyl radical and one alkyl radical attached to an amino radical.

The term "heteroatom," as used herein, refers to oxygen, sulfur, nitrogen and phosphorus.

The terms "heteroaryl" or "heteroaromatic," as used herein, refer to an aromatic that includes at least one sulfur, oxygen, nitrogen or phosphorus in the aromatic ring.

The term "heterocyclic," "heterocyclyl," and cycloheteroalkyl refer to a nonaromatic cyclic group wherein there is at least one heteroatom, such as oxygen, sulfur, nitrogen, or phosphorus in the ring.

Nonlimiting examples of heteroaryl and heterocyclic groups include furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, pyrrole, isopyrrole, pyrazole, imidazole, 1,2,3-triazole, 1,2,4-triazole, oxazole, isoxazole, thiazole, isothiazole, pyrimidine or pyridazine, and pteridinyl, aziridines, thiazole, isothiazole, 1,2,3-oxadiazole, thiazine, pyridine, pyrazine, piperazine, pyrrolidine, oxaziranes, phenazine, phenothiazine, morpholinyl, pyrazolyl, pyridazinyl, pyrazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, adenine, $N^6$-alkylpurines, $N^6$-benzylpurine, $N^6$-halopurine, $N^6$-vinypurine, $N^6$-acetylenic purine, $N^6$-acyl purine, $N^6$-hydroxyalkyl purine, $N^6$-thioalkyl purine, thymine, cytosine, 6-azapyrimidine, 2-mercaptopyrmidine, uracil, $N^5$-alkylpyrimidines, $N^5$-benzylpyrimidines, $N^5$-halopyrimidines, $N^5$-vinylpyrimidine, $N^5$-acetylenic pyrimidine, $N^5$-acyl pyrimidine, $N^5$-hydroxyalkyl purine, and $N^6$-thioalkyl purine, and isoxazolyl. The heteroaromatic group can be optionally substituted as described above for aryl. The heterocyclic or heteroaromatic group can be optionally substituted with one or more substituent selected from halogen, haloalkyl, alkyl, alkoxy, hydroxy, carboxyl derivatives, amido, amino, alkylamino, dialkylamino. The heteroaromatic can be partially or totally hydrogenated as desired. As a nonlimiting example, dihydropyridine can be used in place of pyridine. Functional oxygen and nitrogen groups on the heterocyclic or heteroaryl group can be protected as necessary or desired. Suitable protecting groups are well known to those skilled in the art, and include trimethylsilyl, dimethylhexylsilyl, t-butyldimethylsilyl, and t-butyldiphenylsilyl, trityl or substituted trityl, alkyl groups, acyl groups such as acetyl and propionyl, methanesulfonyl, and p-toluenelsulfonyl. The heterocyclic or heteroaromatic group can be substituted with any moiety that does not adversely affect the reaction, including but not limited to but not limited to those described above for aryl.

The term "host," as used herein, refers to a unicellular or multicellular organism in which the virus can replicate, including but not limited to cell lines and animals, and, preferably, humans. Alternatively, the host can be carrying a part of the viral genome, whose replication or function can be altered by the compounds of the present invention. The term host specifically refers to infected cells, cells transfected with all or part of the viral genome and animals, in particular, primates (including but not limited to chimpanzees) and humans. In most animal applications of the present invention, the host is a human patient. Veterinary applications, in certain indications, however, are clearly contemplated by the present invention (such as for use in treating chimpanzees).

The term "peptide" refers to a natural or synthetic compound containing two to one hundred amino acids linked by the carboxyl group of one amino acid to the amino group of another.

The term "pharmaceutically acceptable salt or prodrug" is used throughout the specification to describe any pharmaceutically acceptable form (such as an ester) compound which, upon administration to a patient, provides the compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on functional moieties of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, or dephosphorylated to produce the active compound. The prodrug forms of the compounds of this invention can possess antiviral activity, can be metabolized to form a compound that exhibits such activity, or both.

II. Active Compound

In one embodiment, the active compound is of Formula (I):

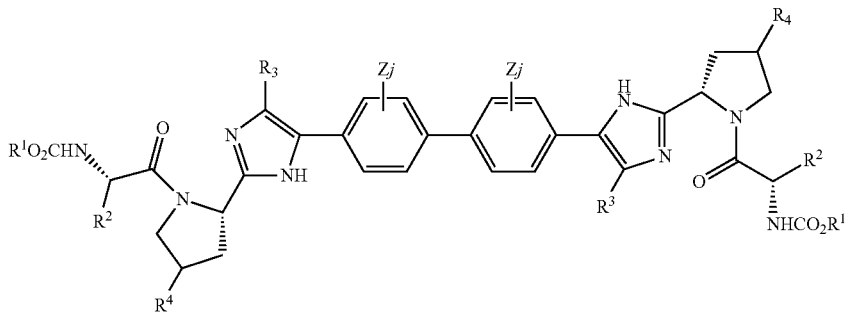

$R^1$ is, independently, H, $C_{1-6}$ alkyl, aryl-$C_{1-6}$-alkyl, $C_{1-6}$ alkyl-aryl, or aryl, $R^2$ is, independently, H, $C_{1-6}$ alkyl, aryl-$C_{1-6}$-alkyl, including $C_{3-6}$ branched alkyl, $C_{1-6}$ alkyl-aryl, aryl, $C_{1-6}$ alkyl-guanidine, $C_{1-6}$ alkylamino, $C_{1-6}$ alkyl-S—$C_{1-6}$ alkyl, $C_{1-6}$ alkylthiol, $C_{1-6}$ alkyl-hydroxy, $C_{1-6}$ alkyl-amide, $C_{1-6}$ alkyl-phenoxy, $C_{1-6}$ alkyl-carboxy heteroaryl, and heteroaryl-$C_{1-6}$ alkyl, wherein aryl rings can be substituted with from 1 to 3 substituents Z as defined herein, $R^3$ is, independently, H or Cl, with the proviso that at least one $R^3$ is Cl, $R^4$ is, independently, H or —S(O)$_x$—$R^1$, with the proviso that at least one $R^4$ is —S(O)$_x$—$R^1$.

Z is selected from the group consisting of $C_{1-8}$ alkyl (including cycloalkyl), lower alkenyl ($C_{2-6}$), lower alkynyl ($C_{2-6}$), heterocyclyl, aryl, heteroaryl, arylalkoxycarbonyl, carboxy, halo (e.g., F, Cl, Br, or I), haloalkyl, —OR', —NR'R", hydroxy, hydroxy-$C_{1-6}$ alkyl, alkoxyalkyl($C_{2-8}$), alkoxycarbonyl, —CF$_3$, —CN, —NO$_2$, —C$_2$R', —SR', —N$_3$, —C(=O)NR'R", —NR'C(=O)R", —C(=O)R', —C(=O)OR', —OC(=O)R', —OC(=O)NR'R", —NR'C(=O)OR", —SO$_2$R', —SO$_2$NR'R", —NR'SO$_2$R", N(R')$_2$, SR', OCOR', N(COR')R', N(COR')COR', and SCOR', Each R' and R" are, independently, H, a lower alkyl ($C_{1-6}$), lower haloalkyl ($C_{1-6}$), lower alkoxy ($C_{1-6}$), lower alkenyl ($C_{2-6}$), lower alkynyl ($C_{2-6}$), lower cycloalkyl ($C_{3-6}$), aryl, heteroaryl, heterocyclyl, alkylaryl, aryl-$C_{1-6}$-alkyl (such as benzyl); or if two R' reside on the same nitrogen atom they can come together to form an alkyl ring ($C_{3-6}$) containing none or one heteroatom independently selected from N, O, and S; wherein the R' groups can be substituted with one or more substituents as defined above, for example, hydroxyalkyl, aminoalkyl, and alkoxyalkyl, j is 0-4, and x is 0-2.

The compounds described herein can be in the form of the R- or S-configuration, or a mixture thereof, including a racemic or diastereomeric mixture thereof.

In one embodiment, one or both of the $R^2$ substituents are phenyl or phenyl substituted with one or more substituents Z as defined herein.

In one embodiment, one, two, or three of the $R^1$ substituents are —CH$_3$.

In one embodiment, each $R^1$ is —CH$_3$ and both of the $R^2$ substituents are phenyl or phenyl substituted with one or more substituents Z as defined herein.

A subset of the compounds of Formula (I) is provided below as Formula (IA):

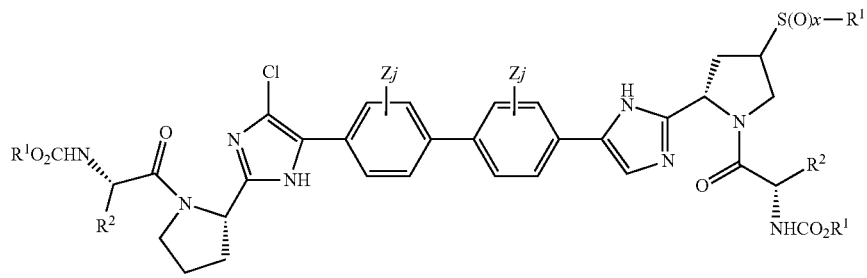

In which $R^1$, $R^2$, Z, R', R", j, and x are as defined with respect to Formula (I).

Representative compounds include the following:

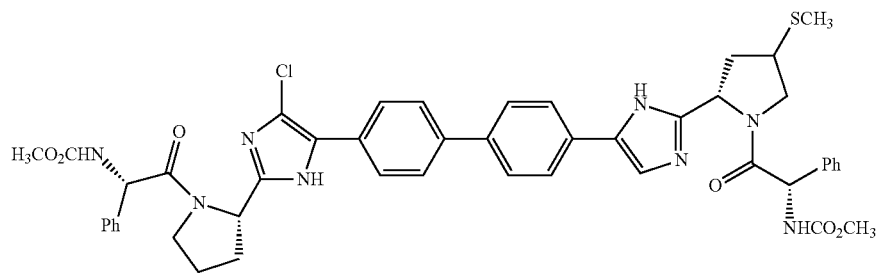

and all other diastereomers thereof, as well as —S(O)—CH$_3$ and —S(O)$_2$—CH$_3$ analogs thereof.
Further representative compounds have one of the following formulas:
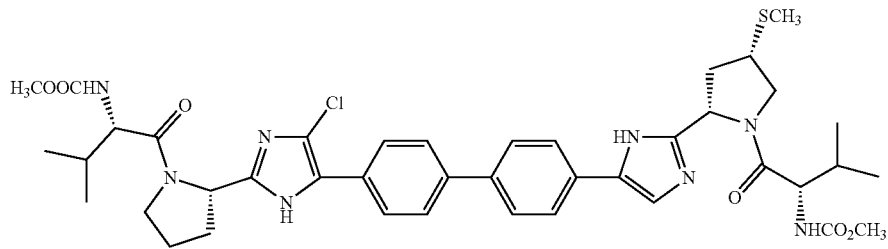
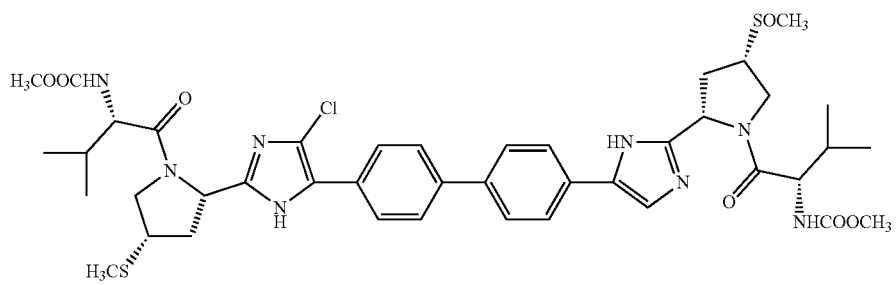
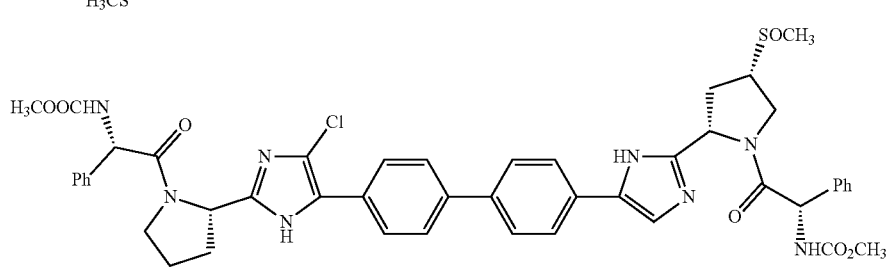
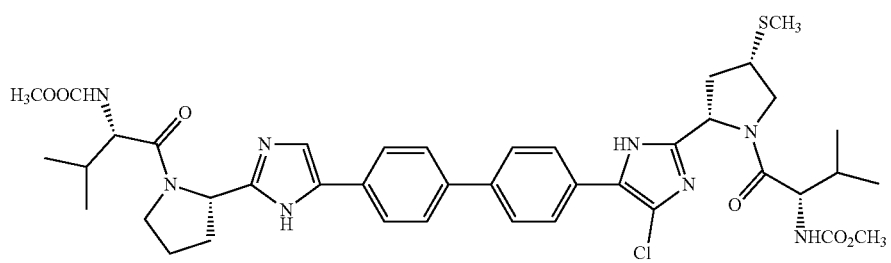
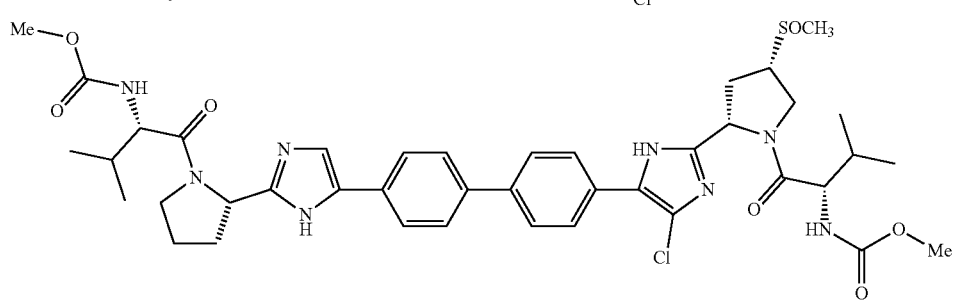
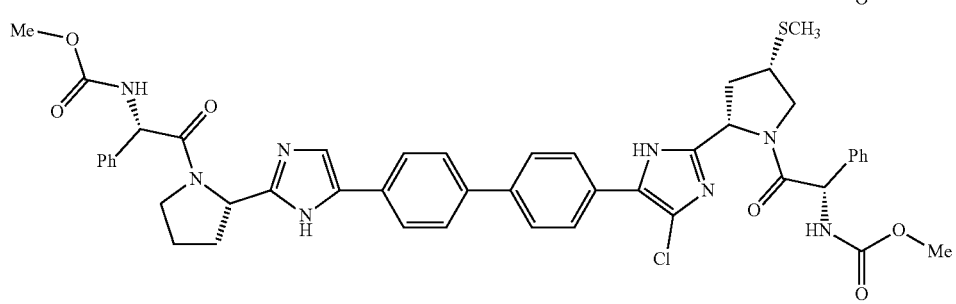

-continued

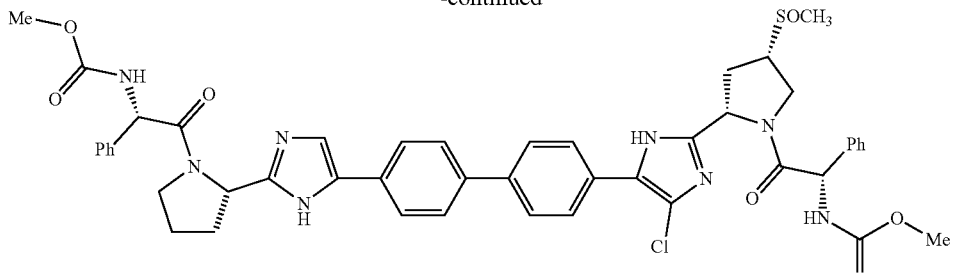

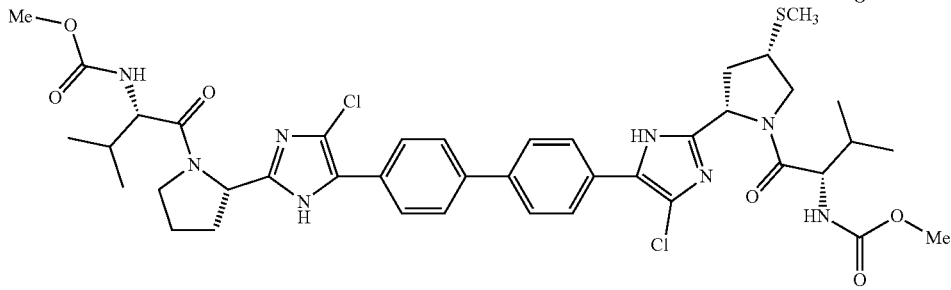

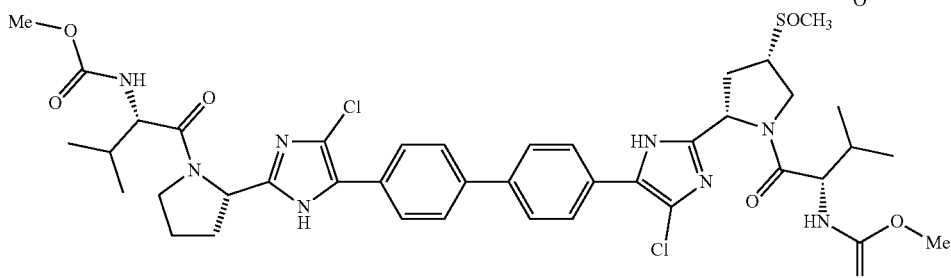

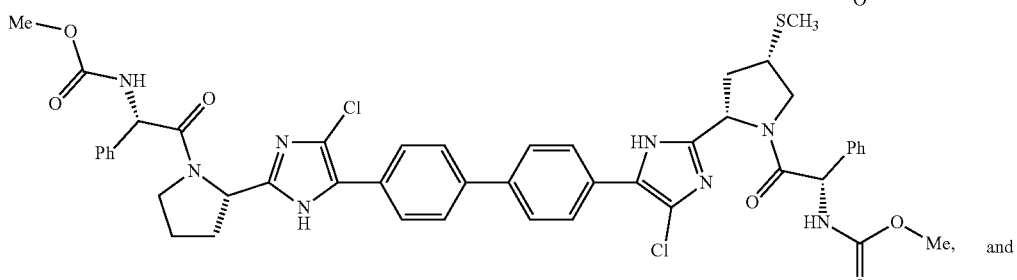

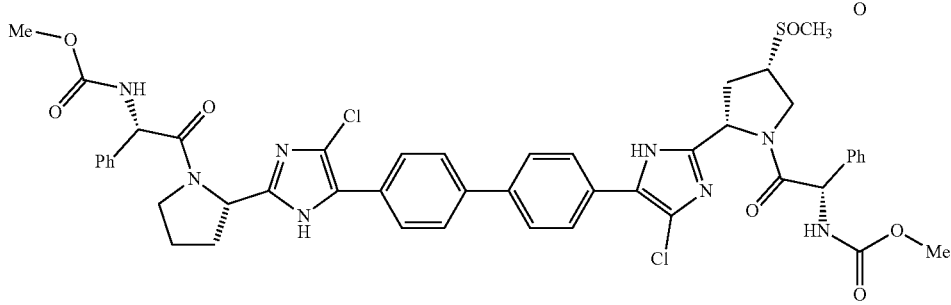

and pharmaceutically-acceptable salts or prodrugs thereof.

III. Stereoisomerism and Polymorphism

The compounds described herein can have asymmetric centers and occur as racemates, racemic mixtures, individual diastereomers or enantiomers, with all isomeric forms being included in the present invention. Compounds of the present invention having a chiral center can exist in and be isolated in optically active and racemic forms. Some compounds can exhibit polymorphism. The present invention encompasses racemic, optically-active, polymorphic, or stereoisomeric forms, or mixtures thereof, of a compound of the invention, which possess the useful properties described herein. The optically active forms can be prepared by, for example, resolution of the racemic form by recrystallization techniques, by synthesis from optically-active starting materials, by chiral synthesis, or by chromatographic separation using a chiral stationary phase or by enzymatic resolution. One can either purify the respective compound, then derivatize the compound to form the compounds described herein, or purify the compound themselves.

Optically active forms of the compounds can be prepared using any method known in the art, including but not limited to by resolution of the racemic form by recrystallization techniques, by synthesis from optically-active starting materials, by chiral synthesis, or by chromatographic separation using a chiral stationary phase.

Examples of methods to obtain optically active materials include at least the following.

i) physical separation of crystals: a technique whereby macroscopic crystals of the individual enantiomers are manually separated. This technique can be used if crystals of the separate enantiomers exist, i.e., the material is a conglomerate, and the crystals are visually distinct;

ii) simultaneous crystallization: a technique whereby the individual enantiomers are separately crystallized from a solution of the racemate, possible only if the latter is a conglomerate in the solid state;

iii) enzymatic resolutions: a technique whereby partial or complete separation of a racemate by virtue of differing rates of reaction for the enantiomers with an enzyme;

iv) enzymatic asymmetric synthesis: a synthetic technique whereby at least one step of the synthesis uses an enzymatic reaction to obtain an enantiomerically pure or enriched synthetic precursor of the desired enantiomer;

v) chemical asymmetric synthesis: a synthetic technique whereby the desired enantiomer is synthesized from an achiral precursor under conditions that produce asymmetry (i.e., chirality) in the product, which can be achieved using chiral catalysts or chiral auxiliaries;

vi) diastereomer separations: a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) first- and second-order asymmetric transformations: a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) kinetic resolutions: this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) enantiospecific synthesis from non-racemic precursors: a synthetic technique whereby the desired enantiomer is obtained from non-chiral starting materials and where the stereochemical integrity is not or is only minimally compromised over the course of the synthesis;

x) chiral liquid chromatography: a technique whereby the enantiomers of a racemate are separated in a liquid mobile phase by virtue of their differing interactions with a stationary phase (including but not limited to via chiral HPLC). The stationary phase can be made of chiral material or the mobile phase can contain an additional chiral material to provoke the differing interactions;

xi) chiral gas chromatography: a technique whereby the racemate is volatilized and enantiomers are separated by virtue of their differing interactions in the gaseous mobile phase with a column containing a fixed non-racemic chiral adsorbent phase;

xii) extraction with chiral solvents: a technique whereby the enantiomers are separated by virtue of preferential dissolution of one enantiomer into a particular chiral solvent;

xiii) transport across chiral membranes: a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

Chiral chromatography, including but not limited to simulated moving bed chromatography, is used in one embodiment. A wide variety of chiral stationary phases are commercially available.

IV. Salt or Prodrug Formulations

In cases where compounds are sufficiently basic or acidic to form stable nontoxic acid or base salts, administration of the compound as a pharmaceutically acceptable salt may be appropriate. Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate and α-glycerophosphate. Suitable inorganic salts can also be formed, including but not limited to, sulfate, nitrate, bicarbonate and carbonate salts.

Pharmaceutically acceptable salts can be obtained using standard procedures well known in the art, for example by reacting a sufficiently basic compound such as an amine with a suitable acid, affording a physiologically acceptable anion. Alkali metal (e.g., sodium, potassium or lithium) or alkaline earth metal (e.g., calcium) salts of carboxylic acids can also be made.

A prodrug is a pharmacological substance that is administered in an inactive (or significantly less active) form and subsequently metabolized in vivo to an active metabolite. Getting more drug to the desired target at a lower dose is often the rationale behind the use of a prodrug and is generally attributed to better absorption, distribution, metabolism, and/or excretion (ADME) properties. Prodrugs are usually designed to improve oral bioavailability, with poor absorption from the gastrointestinal tract usually being the limiting factor. Additionally, the use of a prodrug strategy can increase the selectivity of the drug for its intended target thus reducing the potential for off target effects.

V. Methods of Treatment

Hosts, including but not limited to humans, infected with HCV or a gene fragment thereof, can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

VI. Combination or Alternation Therapy

In one embodiment, the compounds of the invention can be employed together with at least one other antiviral agent, selected from polymerase inhibitors, IMPDH inhibitors, protease inhibitors, and immune-based therapeutic agents.

For example, when used to treat or prevent HCV infection, the active compound or its prodrug or pharmaceutically acceptable salt can be administered in combination or alternation with another anti-HCV including, but not limited to, those of the formulae above. In general, in combination therapy, effective dosages of two or more agents are administered together, whereas during alternation therapy, an effective dosage of each agent is administered serially. The dosage will depend on absorption, inactivation and excretion rates of the drug, as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

Nonlimiting examples of antiviral agents that can be used in combination with the compounds disclosed herein include those in the tables below.

Table of anti-Hepatitis C Compounds in Current Clinical Development

| Drug Name | Drug Category | Pharmaceutical Company |
|---|---|---|
| PEGASYS pegylated interferon alfa-2a | Long acting interferon | Roche |
| INFERGEN interferon alfacon-1 | Interferon, Long acting interferon | InterMune |
| OMNIFERON natural interferon | Interferon, Long acting interferon | Viragen |
| ALBUFERON | Longer acting interferon | Human Genome Sciences |
| REBIF interferon beta-1a | Interferon | Ares-Serono |
| Omega Interferon | Interferon | BioMedicine |
| Oral Interferon alpha | Oral Interferon | Amarillo Biosciences |
| Interferon gamma-1b | Anti-fibrotic | InterMune |
| IP-501 | Anti-fibrotic | Interneuron |
| Merimebodib VX-497 | IMPDH inhibitor (inosine monophosphate dehydrogenase) | Vertex |
| AMANTADINE (Symmetrel) | Broad Antiviral Agent | Endo Labs Solvay |
| IDN-6556 | Apotosis regulation | Idun Pharma. |
| XTL-002 | Monclonal Antibody | XTL |
| HCV/MF59 | Vaccine | Chiron |
| CIVACIR | Polyclonal Antibody Therapeutic vaccine | NABI Innogenetics |
| VIRAMIDINE | Nucleoside Analogue | ICN |
| ZADAXIN (thymosin alfa-1) | Immunomodulator | Sci Clone |
| CEPLENE histamine dihydrochloride | Immunomodulator | Maxim |
| VX 950/ LY 570310 | Protease Inhibitor | Vertex/Eli Lilly |
| ISIS 14803 | Antisense | Isis Pharmaceutical/ Elan |
| IDN-6556 | Caspase inhibitor | Idun Pharmaceuticals, Inc. http://www.idun.com |
| JTK 003 | Polymerase Inhibitor | AKROS Pharma |
| Tarvacin | Anti-Phospholipid Therapy | Peregrine |

Table of anti-Hepatitis C Compounds in Current Clinical Development

| Drug Name | Drug Category | Pharmaceutical Company |
|---|---|---|
| HCV-796 | Polymerase Inhibitor | ViroPharma/Wye |
| CH-6 | Serine Protease | Schering |
| ANA971 | Isatoribine | ANADYS |
| ANA245 | Isatoribine | ANADYS |
| CPG 10101 (Actilon) | Immunomodulator | Coley |
| Rituximab (Rituxam) | Anti-CD20 Monoclonal Antibody | Genetech/IDEC |
| NM283 (Valopicitabine) | Polymerase Inhibitor | Idenix Pharmaceuticals |
| HepX ™-C | Monclonal Antibody | XTL |
| IC41 | Therapeutic Vaccine | Intercell |
| Medusa Interferon | Longer acting interferon | Flamel Technologies |
| E-1 | Therapeutic Vaccine | Innogenetics |
| Multiferon | Long Acting Interferon | Viragen |
| BILN 2061 | Serine Protease | Boehringer - Ingelheim |
| Interferon beta-1a (REBIF) | Interferon | Ares-Serono |

VIII. Pharmaceutical Compositions

Hosts, including but not limited to humans, infected with HCV can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

A preferred dose of the compound for will be in the range of between about 0.01 and about 10 mg/kg, more generally, between about 0.1 and 5 mg/kg, and, preferably, between about 0.5 and about 2 mg/kg, of body weight of the recipient per day. The effective dosage range of the pharmaceutically acceptable salts and prodrugs can be calculated based on the weight of the parent compound to be delivered. If the salt or prodrug exhibits activity in itself, the effective dosage can be estimated as above using the weight of the salt or prodrug, or by other means known to those skilled in the art.

The compound is conveniently administered in unit any suitable dosage form, including but not limited to but not limited to one containing 7 to 300 mg, preferably 70 to 140 mg of active ingredient per unit dosage form. An oral dosage of 5-300 mg is usually convenient.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient can be administered at once, or can be divided into a number of smaller doses to be administered at varying intervals of time.

A preferred mode of administration of the active compound is oral. Oral compositions will generally include an inert diluent or an edible carrier. They can be enclosed in gelatin capsules or compressed into tablets. For the purpose of oral therapeutic administration, the active compound can be incorporated with excipients and used in the form of tablets, troches or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, unit dosage forms can contain various other materials that modify the physical form of the dosage unit, for example, coatings of sugar, shellac, or other enteric agents.

The compound can be administered as a component of an elixir, suspension, syrup, wafer, chewing gum or the like. A syrup can contain, in addition to the active compound(s), sucrose as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories or other antiviral compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents, such as ethylenediaminetetraacetic acid; buffers, such as acetates, citrates or phosphates, and agents for the adjustment of tonicity, such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including but not limited to implants and microencapsulated delivery systems. Biodegradable, biocompatible polymers can be used, such as ethylene vinyl acetate, polyanhydrides, polyglycolic acid, collagen, polyorthoesters and polylactic acid. For example, enterically coated compounds can be used to protect cleavage by stomach acid. Methods for preparation of such formulations will be apparent to those skilled in the art. Suitable materials can also be obtained commercially.

Liposomal suspensions (including but not limited to liposomes targeted to infected cells with monoclonal antibodies to viral antigens) are also preferred as pharmaceutically acceptable carriers. These can be prepared according to methods known to those skilled in the art, for example, as described in U.S. Pat. No. 4,522,811 (incorporated by reference). For example, liposome formulations can be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound is then introduced into the container. The container is then swirled by hand to free lipid material from the sides of the container and to disperse lipid aggregates, thereby forming the liposomal suspension.

The terms used in describing the invention are commonly used and known to those skilled in the art. As used herein, the following abbreviations have the indicated meanings:
ACN acetonitrile
aq aqueous
CDI carbonyldiimidazole
DIPEA diisopropyl ethyl amine (Hünig's base)
DMF N,N-dimethylformamide
DMSO dimethylsulfoxide
EDC 1-ethyl-3-(3-dimethyllaminopropyl)carbodiimide hydrochloride
EtOAc ethyl acetate
h hour
HOBt N-hydroxybenzotriazole
M molar
min minute
Ms mesylate
NCS N-chlorosuccinimide
NBS N-bromosuccinimide
NIS N-iodosuccinimide
Pyr pyridine
rt or RT room temperature
TBAT tetrabutylammonium triphenyldifluorosilicate
TBTU O-(Benzotriazol-1-yl)-N,N,N',N'-tetramethyluronium tetrafluoroborate
TEA triethyl amine
THF tetrahydrofuran
Ts tosylate IX. General Schemes for Preparing Active Compounds Methods for the facile preparation of active compounds are provided. The compounds disclosed herein can be prepared as described in detail below, or by other methods known to those skilled in the art. It will be understood by one of ordinary skill in the art that these schemes are in no way limiting and that variations of detail can be made without departing from the spirit and scope of the present invention.

The various reaction schemes are summarized below.

Scheme 1. is a non-limiting example of the synthesis of active compounds of the present invention, and in particular, a synthetic approach to trisubstituted imidazoles Scheme 1 Synthesis of Trisubstituted Imidazoles Scheme 1. A Non-Limiting Example of the Synthesis of Active Compounds of the Present Invention, and in Particular, a Synthetic Approach to Trisubstituted Imidazoles The general keto-ester IX is prepared from the bis alpha-LG keto compound VIII, in which the LG groups are suitable leaving groups such as I, Br, Cl, OMs, OTs, etc., by displacement with an appropriate cyclic or acyclic amino acid in the presence of an appropriate base, such as sodium hydride, Hünig's base, or TEA at room temperature or mild heating in solvent such as dioxane, THF, or acetonitrile (Scheme 2). Treatment IX with a source of ammonium ion such as ammonium chloride, ammonium bromide, or ammonium acetate in solvent such as xylene, DMF, THF, or toluene with heating for 8-36 h results in the formation of imidazole derivative X.

Broad substitution of the imidazole ring at the carbon or nitrogen atoms can by executed by a variety of methods known to one skilled in the art. A halogen atom can be introduced through a reagent such as NBS, NCS and NIS, and N-fluorobenzenesulfonimide. Suzuki and Stille palladium catalyzed coupling conditions can provide heteroaryl derivatives, alkenes, and alkyne derivatives. Azido or cyano groups can be introduced with reagents such as TMSCN or TMSN$_3$. Nitrogen substitution can be accomplished by acylation, alkylation, or other methods known to one skilled in the art.

Depending on the nature of the amino acid protecting group, it can be removed via strong acid or strong Lewis acid such as HCl, trifluoroacetic acid, or BBr$_3$. Hydrogenolysis or metal reduction can also provide protecting group removal.

The unmasked nitrogen atom from XI can be substituted by acylation, alkylation, or other methods known to one skilled in the art. Ultimately, compounds of type XII can be realized by acylation with an appropriately substituted carboxylic acid in the presence of standard coupling reagent such as HATU, EDCI, or PyBop in the presence of base such as Hunig's base.

Anhydrous solvents were purchased from Aldrich Chemical Company, Inc. (Milwaukee, Wis.) and EMD Chemicals Inc. (Gibbstown, N.J.). Reagents were purchased from commercial sources. Unless noted otherwise, the materials used in the examples were obtained from readily available commercial suppliers or synthesized by standard methods known to one skilled in the art of chemical synthesis. Melting points (mp) were determined on an Electrothermal digit melting point apparatus and are uncorrected. $^1$H and $^{13}$C NMR spectra were taken on a Varian Unity Plus 400 spectrometer at room temperature and reported in ppm downfield from internal tetramethylsilane. Deuterium exchange, decoupling experiments or 2D-COSY were performed to confirm proton assignments. Signal multiplicities are represented by s (singlet), d (doublet), dd (doublet of doublets), t (triplet), q (quadruplet), br (broad), bs (broad singlet), m (multiplet). All J-values are in Hz. Mass spectra were determined on a Micromass Platform LC spectrometer using electrospray techniques. Elemental analyses were performed by Atlantic Microlab Inc. (Norcross, Ga.). Analytic TLC was performed on Whatman LK6F silica gel plates, and preparative TLC on Whatman PK5F silica gel plates. Column chromatography was carried out on Silica Gel or via reverse-phase high performance liquid chromatography.

Example 1

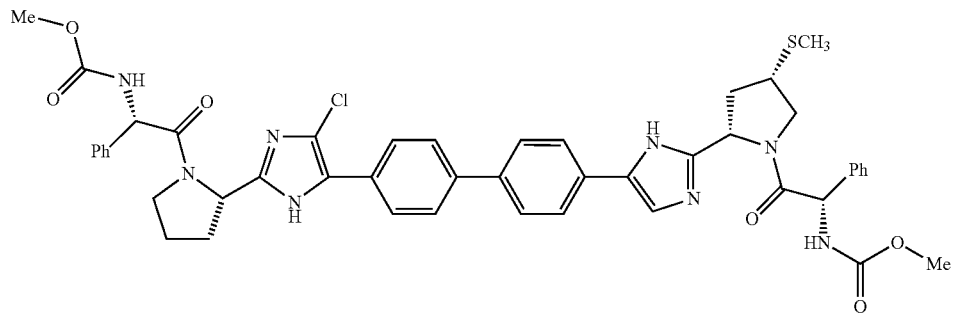

30

The present invention is further illustrated in the following non-limiting examples. Scheme 1 and Examples 1-3 show preparative methods for synthesizing HCV inhibitor compounds, and Examples 4-8 show methods for their biological evaluation. It will be understood by one of ordinary skill in the art that these examples are in no way limiting and that variations of detail can be made without departing from the spirit and scope of the present invention.

SPECIFIC EXAMPLES

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The present compounds can also be used as intermediates in subsequent examples to produce additional compounds of the present invention. No attempt has necessarily been made to optimize the yields obtained in any of the reactions. One skilled in the art would know how to increase such yields through routine variations in reaction times, temperatures, solvents and/or reagents.

The Procedure for Synthesis of Compound 30

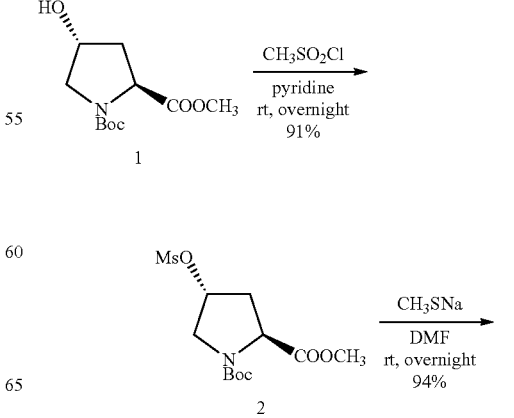

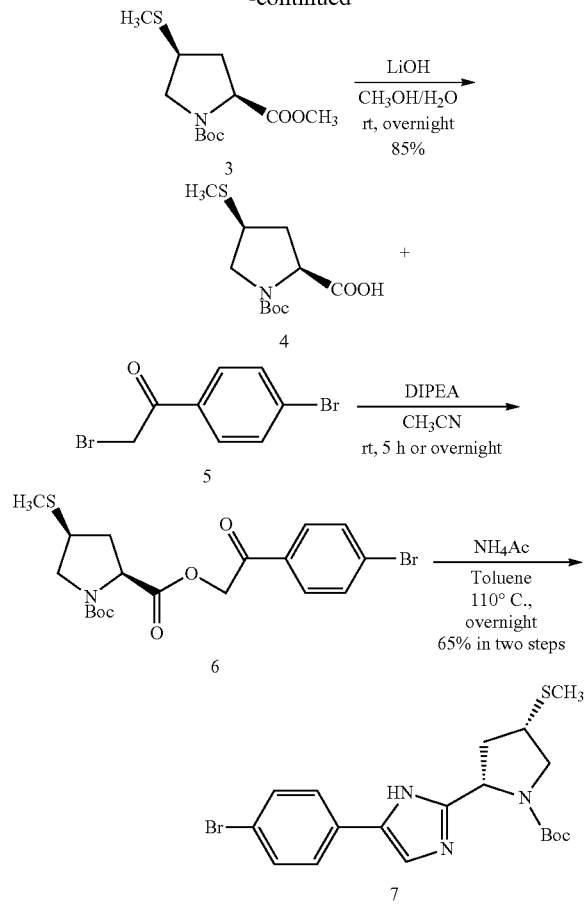

(2S,4S)-1-(tert-butoxycarbonyl)-4-(methylthio)pyrrolidine-2-carboxylic acid 4

A solution of 4-methylthioproline 3 (5 g, 18.2 mmol) in methanol (40 mL) and water (40 mL) was added lithium hydroxide (5 g, 0.2 mol) and the resulting reaction mixture was stirred overnight. The methanol was evaporated under vacuum, extracted with ethyl acetate, and the separated organic layer was discarded. The aqueous layer was acidified with 6 N HCl, extracted with ethyl acetate, washed with water, dried over sodium sulfate, filtered, and concentrated to afford 4 g, 85%.

(2S,4S)-tert-butyl 2-(5-(4-bromophenyl)-1H-imidazol-2-yl)-4-(methylthio)pyrrolidine-1-carboxylate 7

To a solution of carboxylic acid derivative 4 (2 g, 7.7 mmol) in acetonitrile (10 mL) was added 2-bromo-1-(4-bromophenyl)ethanone 5 (2 g, 7.2 mmol) and DIPEA (1.32 mL, 7.57 mmol) at room temperature and the resulting reaction mixture was stirred overnight. At 18 h the reaction was poured into water, extracted with ethyl acetate (20 mL×2), dried over sodium sulfate, filtered, and concentrated. The desired compound 6 was used for next reaction without any purification.

The crude ester 6 was diluted with toluene (20 mL) and ammonium acetate (4 g) was added. The resulting reaction was heated at 110° C. overnight, diluted with water, extracted with ethyl acetate, dried over sodium sulfate, filtered, concentrated and purified by silica gel chromatography with ethyl acetate:hexane (1:1) to give a white solid, 2 g, 64%.

(2S,4R)-1-tert-butyl 2-methyl 4-((methylsulfonyl)oxy)pyrrolidine-1,2-dicarboxylate 2

A solution of N-Boc-trans-4-hydroxy-L-proline (15 g, 61.1 mmol) in pyridine (72 mL) was added methanesulfonyl chloride (5.77 ml, 74.5 mmol) at 0° C. and the reaction was stirred at the same temperature for 4 h, warmed to room temperature and continued to stir overnight. The solvent was gently removed by vacuum then diluted with ethyl acetate (60 mL), washed with 1N aqueous HCl (two times), and the second washing was tested with pH paper to confirm that it remained acidic. Then the organic layer was washed with water, aqueous sodium bicarbonate, water, dried over sodium sulfate, filtered, concentrated, the residue was used for next reaction without further purification, 18 g, 91%.

(2S,4S)-1-tert-butyl 2-methyl 4-(methylthio)pyrrolidine-1,2-dicarboxylate 3

A solution of 4-methylsulfonyoxyproline 2 (4 g, 12.3 mmol) in dry DMF (15 mL) was added sodium thiomethoxide (1 g, 14.2 mmol) at room temperature, then stirred overnight, poured into water (40 mL), extracted with ethyl acetate (30 mL×2), washed with water, dried over sodium sulfate, filtered, and concentrated to give 3.2 g, 94% (this material may be purified by a short column of silica gel with ethyl acetate:hexane (1:1) or used crude directly in the next step).

Scheme 2. Synthesis of intermediate 12

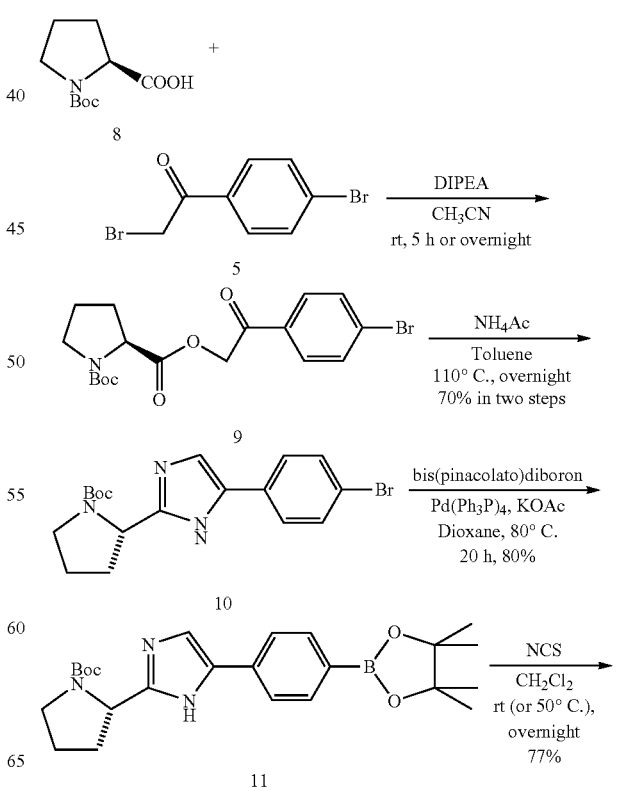

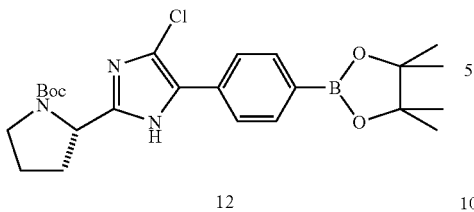

(S)-tert-butyl 2-(5-(4-bromophenyl)-1H-imidazol-2-yl)pyrrolidine-1-carboxylate 10

DIPEA (9.7 mL, 55.6 mmol) was added dropwise to a solution of 2-bromo-1-(4-bromophenyl)ethanone 5 (15 g, 53.9 mmol) and 1-(tert-butoxycarbonyl)-L-proline (12 g, 55.7 mol) in acetonitrile (100 mL) at 5° C. The resulting yellow solution was allowed to warm to room temperature and stirred overnight. The mixture was washed with water (20 mL), saturated sodium bicarbonate solution (20 mL×2), brine (20 mL), dried over Na$_2$SO$_4$ and evaporated under vacuum to give yellow solid 9; the residue was used for next reaction without any purification.

The residue 9 was diluted with toluene (200 mL) and ammonium acetate (20 g) was added. The resulting mixture was heated at 130° C. for 24 h. After cooling, the mixture was poured into with water, extracted with ethyl acetate (30 mL×3). The combined organics were washed with water, saturated sodium bicarbonate, water, dried over Na$_2$SO$_4$, filtered and concentrated. The residue was purified by silica gel chromatography with ethyl acetate: hexane=20:100 to 50:50 to give a white solid, 14.8 g, 70%. In addition, the compound can be purified by suspension in a solvent of hexane: methyl acetate (50:20), then filtered and washed with same solvent to get yellow solid. The purity is good enough for the next reaction.

(S)-tert-butyl 2-(5-(4-(4,4,5,5-tetramethyl-1,3,2-dioxaborolan-2-yl)phenyl)-1H-imidazol-2-yl)pyrrolidine-1-carboxylate 11

A mixture of compound 10 (4 g, 10.2 mmol), bis(pinacolato)diboron (5.44, 21.4 mmol), potassium acetate (2.56 g, 26.08 mmol) and tetrakis(triphenylphosphine)palladium(0) (480 mg, 0.41 mmol) in 1,4-dioxane (60 mL) was stirred at 80° C. under nitrogen for 20 h. After the starting material was consumed, the mixture was filtered; the filtrate was concentrated under vacuum. The residue was partitioned with dichloromethane and water, the water was extracted with dichloromethane (20 mL×2). The organic layers were combined, dried over sodium sulfate, filtered, concentrated and purified by silica gel chromatography with ethyl acetate: hexane (10:100 to 50:50) to give 3.6 g, 80%.

(S)-tert-butyl 2-(4-chloro-5-(4-(4,4,5,5-tetramethyl-1,3,2-dioxaborolan-2-yl)phenyl)-1H-imidazol-2-yl)pyrrolidine-1-carboxylate 12

To a solution of compound 11 (0.61 g, 1.38 mmol) in dichloromethane (5 mL) was added NCS (0.31 g, 2.32 mmol), and the resulting reaction mixture was stirred overnight. Three to four portions of NCS (0.1 g) were added between 16 and 24 h to push the reaction completion. The reaction mixture was poured into water, extracted with dichloromethane (10 mL×3). The combined organic layer was washed with saturated sodium bicarbonate, sodium hydrosulfite, water, dried over sodium sulfate, filtered, concentrated and purified by silica gel chromatography with ethyl acetate:hexane (1:5 to 1:1) to give 500 mg, 77%.

Scheme 3. Synthesis of 30

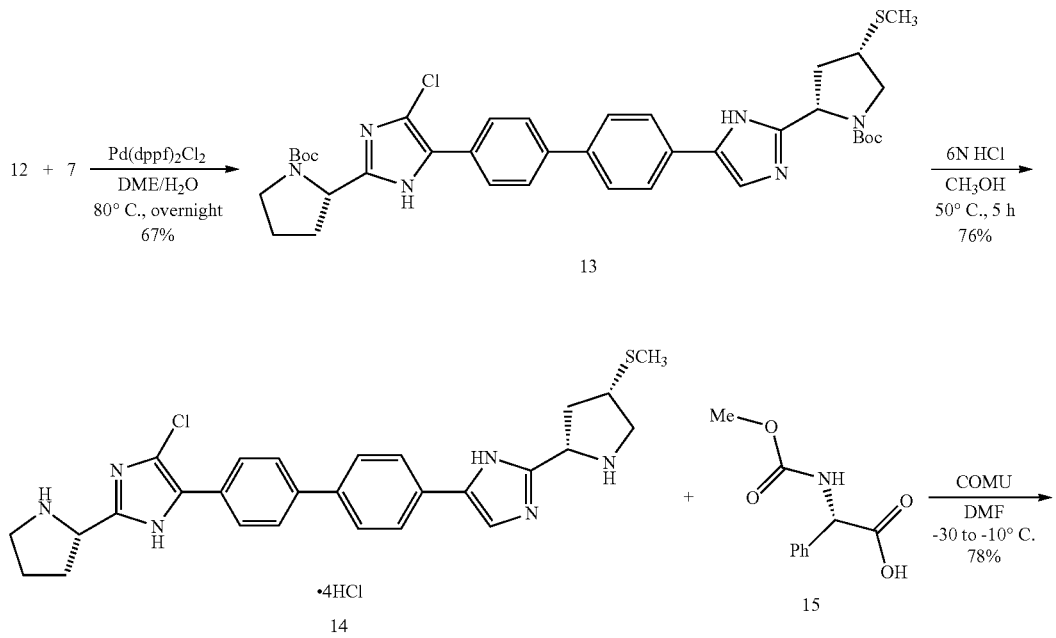

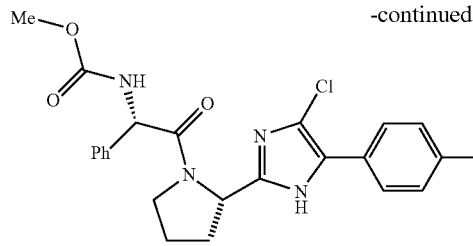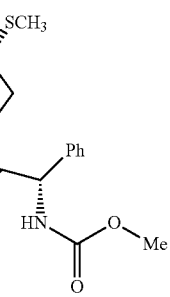

30

(2S,4S)-tert-butyl 2-(5-(4'-(2-((S)-1-(tert-butoxycarbonyl)pyrrolidin-2-yl)-4-chloro-1H-imidazol-5-yl)-[1,1'-biphenyl]-4-yl)-1H-imidazol-2-yl)-4-(methylthio)pyrrolidine-1-carboxylate 13

A mixture of compound 7 (0.47 g, 1.07 mmol) and compound 12 (0.5 g, 1.05 mmol), sodium bicarbonate (0.383 g, 4.55 mmol), diethoxymethane (30 mL), water (9 mL), [1,1'-bis(diphenylphosphino)ferrocene] dichloropalladium (II) (139.09 mg, 0.19 mmol) were heated at 80° C. with stirring overnight under nitrogen. At 18 h the reaction was cooled, poured into water, extracted with ethyl acetate, dried over sodium sulfate, filtered, concentrated and purified by silica gel chromatography with ethyl acetate:hexane (1:1) to give 0.5 g, 67%.

4-chloro-5-(4'-(2-((2S,4S)-4-(methylthio)pyrrolidin-2-yl)-1H-imidazol-5-yl)-[1,1'-biphenyl]-4-yl)-2-((S)-pyrrolidin-2-yl)-1H-imidazole.4HCl 14

A solution of compound 13 (500 mg, 0.708 mmol) in methanol (5 mL) was added 6N HCl (3 mL) at rt. The reaction was warmed to 50° C. for 5 h, The resulting slurry was evaporated and co-evaporated with ethanol for 3 times, filtered, washed with small amount of acetonitrile to obtain yellow solid (dry enough for next reaction) 350 mg, 76%.

(S)-2-((methoxycarbonyl)amino)-2-phenylacetic acid 15

Na$_2$CO$_3$ (1.83 g, 17.2 mmol) was added to a solution NaOH (33 mL of 1M/H$_2$O, 33 mmol) and L-phenylglycine (5.0 g, 33.29 mmol), then the resulting solution was cooled with ice bath, Methyl chloroformate (2.8 mL, 36.1 mmol) was added dropwise to the cooled solvent. After completion of addition, the reaction mixture was stirred at rt for 3.25 hr. The reaction mixture was washed with ether (30 mL×3), and the aqueous phase was cooled with ice bath and acidified with concentrated HCl to a pH region of 1-2, and extracted with CH$_2$Cl$_2$ (30 mL×3), dried over sodium sulfate and concentrated under vacuum to afford white solid, 6.2 g, 90%.

Methyl ((S)-2-((2S,4S)-2-(5-(4'-(4-chloro-2-((S)-1-((S)-2 ((methoxycarbonyl)amino)-2-phenylacetyl)pyrrolidin-2-yl)-1H-imidazol-5-yl)-[1,1'-biphenyl]-4-yl)-1H-imidazol-2-yl)-4-(methylthio)pyrrolidin-1-yl)-2-oxo-1-phenylethyl)carbamate 30

To a stirred solution of 14 (50 mg, 0.076 mmol) and (S)-2-((methoxycarbonyl)amino)-2-phenylacetic acid (48 mg, 0.23 mmol) in DMF (2 mL) at −30° C. was added DIPEA (81.5 μL, 0.46 mmol) then COMU* (98.25 mg, 0.23 mmol) was added. The reaction mixture was stirred at −20° C. to −10° C. for 2-2.5 h (The reaction should be one major spot by TLC then quench the reaction). Water (1 mL) was added to the cold reaction and the resulting solution was extracted with ethyl acetate (10 mL×2). The combined organics were washed with water, saturated sodium bicarbonate, saturated sodium chloride, dried over sodium sulfate, and purified with silica gel chromatography with dichloromethane:methanol=100:1 to 100:5 to give a pale yellow solid, 53 mg, 78%.

Figure 2:
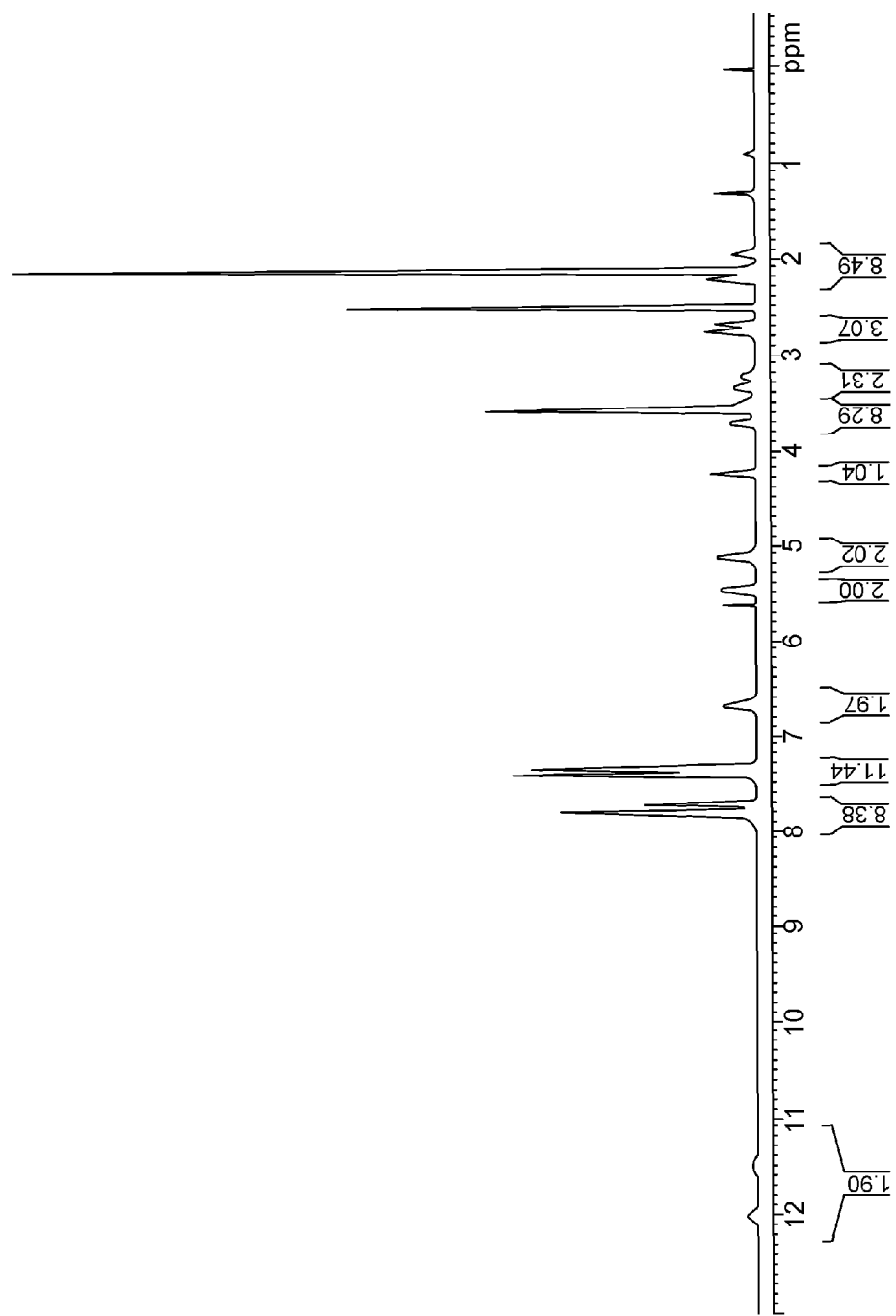
FIG. 2 is a $^1$H NMR spectrum of compound 30.

The $^{13}$C and $^1$H NMR spectra for compound 30 are shown in FIGS. 1 and 2, respectively.

*1-Cyano-2-ethoxy-2-oxoethylideneaminooxy) dimethylaminomorpholino carbenium hexafluorophosphate (1075198-30-9)

The Synthesis of (S)-2-(((methylperoxy)methyl)amino)-2-phenylacetic acid[1]

L-α-phenylglycine (4 g, 26.46 mmol) was dissolved in THF (80 mL) followed by the addition of sodium bicarbonate (6.68 g, 79.54 mmol) in water (80 mL) then added methylchloroformate (2.25 mL, 29.18 mmol) under ice-bath cooling. The reaction mixture was stirred at room temperature overnight. The mixture was acidified to pH 2-3 with 6N HCl, then concentrated in vacuo to remove THF. The aqueous layer was extracted with ethyl acetate (20 mL×2), the organic layer was dried over sodium sulfate, filtered, concentrated to afford the pale-yellow solid, triturated several times with a mixture solvent of ethyl acetate and hexane (V/V 20/60) to get white solid, 4.73 g, 84%.

(1) (S)-2-(((methylperoxy)methyl)amino)-2-phenylacetic acid using sodium hydroxide method gave a trace amount of racemization when synthesized the final compound. The sodium bicarbonate method may give a complete single isomer.

Example 2

Cellular Toxicity Assays

The toxicity of the compounds was assessed in Vero, human PBM, CEM (human lymphoblastoid), MT-2, and HepG2 cells, as described previously (see Schinazi R. F., Sommadossi J.-P., Saalmann V., Cannon D. L., Xie M.-Y., Hart G. C., Smith G. A. & Hahn E. F. *Antimicrob. Agents Chemother.* 1990, 34, 1061-67). Cycloheximide was included as positive cytotoxic control, and untreated cells exposed to solvent were included as negative controls. The cytotoxicity $IC_{50}$ was obtained from the concentration-response curve using the median effective method described previously (see Chou T.-C. & Talalay P. *Adv. Enzyme Regul.* 1984, 22, 27-55; Belen'kii M. S. & Schinazi R. F. *Antiviral Res.* 1994, 25, 1-11).

Example 3

Mitochondrial Toxicity Assays in HepG2 Cells i) Effect of Compounds on Cell Growth and Lactic Acid Production:

The effect on the growth of HepG2 cells can be determined by incubating cells in the presence of 0 μM, 0.1 μM, 1 μM, 10 μM and 100 μM drug. Cells ($5\times10^4$ per well) can be plated into 12-well cell culture clusters in minimum essential medium with nonessential amino acids supplemented with 10% fetal bovine serum, 1% sodium pyruvate, and 1% penicillin/streptomycin and incubated for 4 days at 37° C. At the end of the incubation period the cell number can be determined using a hemocytometer. Also taught by Pan-Zhou X-R, Cui L, Zhou X-J, Sommadossi J-P, Darley-Usmer V M. "Differential effects of antiretroviral nucleoside analogs on mitochondrial function in HepG2 cells" Antimicrob. Agents Chemother. 2000; 44: 496-503. To measure the effects of the compounds on lactic acid production, HepG2 cells from a stock culture can be diluted and plated in 12-well culture plates at $2.5\times10^4$ cells per well. Various concentrations (0 μM, 0.1 μM, 1 μM, 10 μM and 100 μM) of compound were added, and the cultures can be incubated at 37° C. in a humidified 5% $CO_2$ atmosphere for 4 days. At day 4, the number of cells in each well can be determined and the culture medium collected. The culture medium is then filtered, and the lactic acid content in the medium can be determined using a colorimetric lactic acid assay (Sigma-Aldrich). Since lactic acid product can be considered a marker for impaired mitochondrial function, elevated levels of lactic acid production detected in cells grown in the presence of test compounds would indicate a drug-induced cytotoxic effect.

ii) Effect on Compounds on Mitochondrial DNA Synthesis:

a real-time PCR assay to accurately quantify mitochondrial DNA content has been developed (see Stuyver L J, Lostia S, Adams M, Mathew J S, Pai B S, Grier J, Tharnish P M, Choi Y, Chong Y, Choo H, Chu C K, Otto M J, Schinazi R F. Antiviral activities and cellular toxicities of modified 2',3'-dideoxy-2',3'-didehydrocytidine analogs. Antimicrob. Agents Chemother. 2002; 46: 3854-60). This assay can be used in all studies described in this application that determine the effect of compounds on mitochondrial DNA content. In this assay, low-passage-number HepG2 cells are seeded at 5,000 cells/well in collagen-coated 96-well plates. Test compounds are added to the medium to obtain final concentrations of 0 μM, 0.1 μM, 10 μM and 100 μM. On culture day 7, cellular nucleic acids are prepared by using commercially available columns (RNeasy 96 kit; Qiagen). These kits co-purify RNA and DNA, and hence, total nucleic acids are eluted from the columns. The mitochondrial cytochrome c oxidase subunit II (COXII) gene and the β-actin or rRNA gene are amplified from 5 μl of the eluted nucleic acids using a multiplex Q-PCR protocol with suitable primers and probes for both target and reference amplifications. For COXII the following sense, probe and antisense primers are used, respectively: 5'-TGCCCGCCATCATCCTA-3', 5'-tetrachloro-6-carboxyfluorescein-TCCTCATCGCCCTCCCATCCC-TAMRA-3' and 5'-CGTCTGTTATGTAAAGGATGCGT-3'. For exon 3 of the β-actin gene (GenBank accession number E01094) the sense, probe, and antisense primers are 5'-GCGCGGC-TACAGCTTCA-3', 5'-6-FAMCACCACGGC-CGAGCGGGATAMRA-3' and 5'-TCTCCTTAATGT-CACGCACGAT-3', respectively. The primers and probes for the rRNA gene are commercially available from Applied Biosystems. Since equal amplification efficiencies are obtained for all genes, the comparative CT method can be used to investigate potential inhibition of mitochondrial DNA synthesis. The comparative CT method uses arithmetic formulas in which the amount of target (COXII gene) is normalized to the amount of an endogenous reference (the β-actin or rRNA gene) and is relative to a calibrator (a control with no drug at day 7). The arithmetic formula for this approach is given by 2-ΔΔCT, where ΔΔCT is (CT for average target test sample−CT for target control)−(CT for average reference test−C T for reference control) (see Johnson M R, K Wang, J B Smith, M J Heslin, R B Diasio. Quantitation of dihydropyrimidine dehydrogenase expression by real-time reverse transcription polymerase chain reaction. Anal. Biochem. 2000; 278:175-184). A decrease in mitochondrial DNA content in cells grown in the presence of drug would indicate mitochondrial toxicity.

Example 4

Mitochondrial Toxicity Assays in Neuro2A Cells

To estimate the potential of the compounds of this invention to cause neuronal toxicity, mouse Neuro2A cells (American Type Culture Collection 131) were used as a model system (see Ray A S, Hernandez-Santiago B I, Mathew J S, Murakami E, Bozeman C, Xie M Y, Dutschman G E, Gullen E, Yang Z, Hurwitz S, Cheng Y C, Chu C K, McClure H, Schinazi R F, Anderson K S. Mechanism of anti-human immunodeficiency virus activity of beta-D-6-cyclopropylamino-2',3'-didehydro-2',3'-dideoxyguanosine. *Antimicrob. Agents Chemother.* 2005, 49, 1994-2001). The concentrations necessary to inhibit cell growth by 50% ($CC_{50}$) were measured using the 3-(4,5-dimethyl-thiazol-2-yl)-2,5-diphenyltetrazolium bromide dye-based assay, as described. Perturbations in cellular lactic acid and mitochondrial DNA levels at defined concentrations of drug were carried out as described above. In all experiments, ddC and AZT were used as control nucleoside analogs.

Example 5

Assay for Bone Marrow Cytotoxicity

Primary human bone marrow mononuclear cells can be obtained commercially from Cambrex Bioscience (Walkersville, Md.). CFU-GM assays can be carried out using a bilayer soft agar in the presence of 50 units/mL human recombinant granulocyte/macrophage colony-stimulating factor, while BFU-E assays use a methylcellulose matrix containing 1 unit/mL erythropoietin (see Sommadossi J P, Carlisle R. Toxicity of 3'-azido-3'-deoxythymidine and 9-(1, 3-dihydroxy-2-propoxymethyl) guanine for normal human hepatopoietic progenitor cells in vitro. Antimicrob. Agents Chemother. 1987; 31: 452-454; Sommadossi, J P, Schinazi, R F, Chu, C K, and Xie, M Y. Comparison of cytotoxicity of the (−) and (+) enantiomer of 2',3'-dideoxy-3'-thiacytidine in normal human bone marrow progenitor cells. Biochem. Pharmacol. 1992; 44:1921-1925). Each experiment can be performed in duplicate in cells from three different donors. AZT can be used as a positive control. Cells can be incubated in the presence of the compound for 14-18 days at 37° C. with 5% $CO_2$, and colonies of greater than 50 cells can be counted using an inverted microscope to determine $IC_{50}$. The 50% inhibitory concentration ($IC_{50}$) can be obtained by least-squares linear regression analysis of the logarithm of drug concentration versus BFU-E survival fractions. Statistical analysis can be performed with Student's t test for independent non-paired samples.

Example 6

HCV Replicon Assay[1]

Huh 7 Clone B cells containing HCV Replicon RNA would be seeded in a 96-well plate at 5000 cells/well, and the compounds tested at 10 µM in triplicate immediately after seeding. Following five days incubation (37° C., 5% $CO_2$), total cellular RNA was isolated by using versaGene RNA purification kit from Gentra. Replicon RNA and an internal control (TaqMan rRNA control reagents, Applied Biosystems) were amplified in a single step multiplex Real Time RT-PCR Assay. The antiviral effectiveness of the compounds was calculated by subtracting the threshold RT-PCR cycle of the test compound from the threshold RT-PCR cycle of the no-drug control (ΔCt HCV). A ΔCt of 3.3 equals a 1-log reduction (equal to 90% less starting material) in Replicon RNA levels. The cytotoxicity of the compounds was also calculated by using the ΔCt rRNA values. 2'-C-Me-C was used as the positive control. To determine $EC_{90}$ and $IC_{50}$ values[2], ΔCt: values were first converted into fraction of starting material[3] and then were used to calculate the % inhibition.

REFERENCES

1. Stuyver L et al., Ribonucleoside analogue that blocks replication or bovine viral diarrhea and hepatitis C viruses in culture. Antimicrob. *Agents Chemother.* 2003, 47, 244-254.
2. Reed I J & Muench H, A simple method or estimating fifty percent endpoints. *Am. J. Hyg.* 27: 497, 1938.
3. Applied Biosystems Handbook Median Effective concentrations ($EC_{50}$) ranges against HCV 1b are as follow:
A=1-1 µM
B=100-999 nM
C=1-99 nM
D=<1 nM Example 7

Metabolic Study of NS5A Inhibitors Compound A and Compound B in Human Liver Microsomes Purpose
To identify the metabolites of Compound 30 in Human Liver Microsomes.

Chemicals
Methanol and acetonitrile were purchased from (Fisher Scientific)
Formic acid was purchased from ACROS Organics.
Water was purified and deionized.

Instrumentation
The HPLC system was an Ultimate 3000 modular LC system consisting of two ternary pump, vacuum degasser, thermostated autosampler, and thermostated column compartment (Dionex Corporation; Sunnyvale, Calif.). A TSQ Quantum Ultra triple quadrupole mass spectrometer (Thermo Scientific, Waltham, Mass., USA.) was used for detection. Thermo Xcalibur software version 2.0 was used to operate HPLC, the mass spectrometer and to perform data analyses.

Method Summary & Results
Compounds (1 µM final concentration) were incubated with human liver microsomes in potassium phosphate buffer. The microsomal protein concentration in the assay was 1 mg/mL and the final percent DMSO was less than 0.2%. Reaction was started by the addition of NADPH and stopped at 60 min by 200 µL of 80% ice cold MeOH (containing 100 nM of the internal standard RS-1174). The samples were qualitatively and quantitatively analyzed by LC-MS/MS.

Gradient separation was performed on a Hypersil GOLD column (100×1.0 mm) with a 3 µm particle size (Thermo Electron, Waltham, Mass.). The mobile phase A consisted of water containing 0.1% formic acid and B consisted of acetonitrile. Mobile phase B was increased from 15% to 100% in 8 min, and kept at 100% for 2 min. The flow rate was maintained at 50 µL/min and a 25 µL injection volume was used. The autosampler was maintained at 4° C., and the column was maintained at 30° C.

The first 3.0 min of the analysis was diverted to waste. The mass spectrometer was operated in negative ionization mode with a spray voltage of 3.0 kV, sheath gas at 50 (arbitrary units), ion sweep gas at 0.2 (arbitrary units), auxiliary gas at 5 (arbitrary units), and a capillary temperature of 300° C. The collision cell pressure was maintained at 1.5 mTorr. The precursor and product ion transitions were listed in the following Table.

Example 8

Evaluation of HCV Activity and Cytotoxicity of Lead Compounds

While not wishing to be bound to a particular theory, among the thiomethyl containing compounds that may provide multiple biologically active entities in vivo, the best combination of anti-HCV activity and lack of cytotoxicity appears to be found in the compounds that contain at least one thiomethyl group and zero to two chlorine atoms.

Overall, those compounds which contained at least one thiomethyl and at least one chlorine atom, ideally with phenylalanine attached to the pyrrolidine ring, provided the compounds with the best toxicity and anti-HCV activity profile.

The activity and cytotoxicity of a series of compounds within the scope of Formula (I) was evaluated using the protocols in the examples above, and the data is summarized in the table below.

| Structure | HCV | | Cytotoxicity (IC$_{50}$ μM) | | |
|---|---|---|---|---|---|
| | EC$_{50}$ (nM) | EC$_{90}$ (nM) | PBM | CEM | Vero |
| Compound 30 | 6.1 pM | 15.1 pM | >100 | >100 | >100 |
| Compound 42 | 13.9 pM | 26.3 pM | 60.0 | 3.1 | 34.5 |
| Compound 43 | 0.4 | 2.3 | 18.6 | 12.9 | >100 |
| Compound 44 | 0.2 | 1.1 | 89.7 | 3.6 | >100 |
| Compound 45 | 16.3 pM | 31.6 pM | 27.2 | 5.2 | 14.4 |

-continued

| Structure | HCV | | Cytotoxicity (IC$_{50}$ μM) | | |
|---|---|---|---|---|---|
| | EC$_{50}$ (nM) | EC$_{90}$ (nM) | PBM | CEM | Vero |
| Compound 46 | 0.06 | .3 | 13.6 | 3.7 | 45.8 |
| Compound 47 | 4 pM | 23.1 pM | >100 | >100 | >100 |
| Compound 48 | 0.07 | 0.5 | 67.6 | 1.8 | >100 |
| Compound 49 | 3.4 pM | 69.9 pM | 24.3 | 2.5 | >100 |
| Compound 50 | 0.07 | 0.5 | 21.9 | 1.3 | >100 |

-continued

| Structure | HCV EC$_{50}$ (nM) | EC$_{90}$ (nM) | Cytotoxicity (IC$_{50}$ μM) PBM | CEM | Vero |
|---|---|---|---|---|---|
| 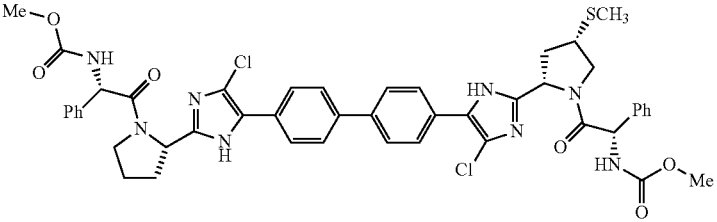 Compound 51 | 7.7 pM | 19.1 pM | >100 | >100 | >100 |
| 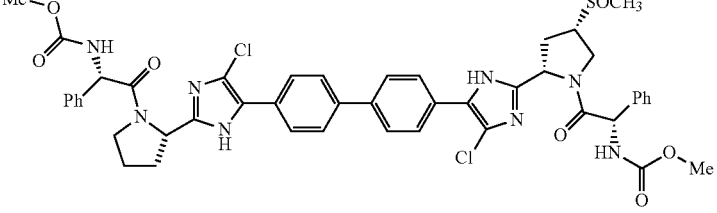 Compound 52 | 0.06 | 0.2 | 83.9 | 7.1 | >100 |

The present invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

Various publications are cited herein, the disclosures of which are incorporated by reference in their entireties.

We claim:
1. A compound of Formula (I):

Formula (I)

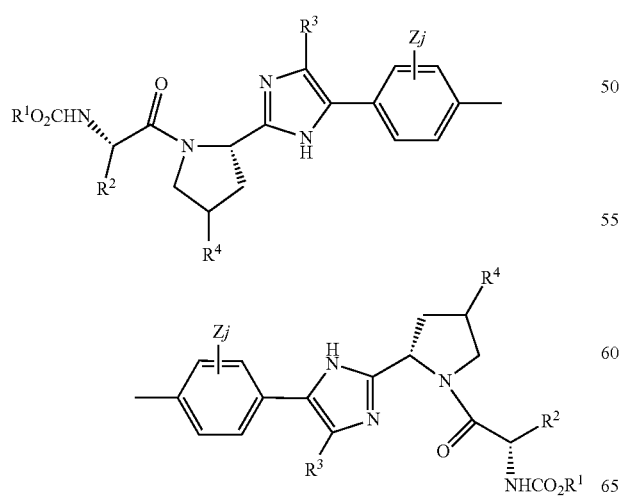

$R^1$ is, independently, H, $C_{1-6}$ alkyl, aryl-$C_{1-6}$-alkyl, $C_{1-6}$ alkyl-aryl, or aryl, $R^2$ is, independently, H, aryl-$C_{1-6}$-alkyl, $C_{1-6}$ alkyl-aryl, aryl, $C_{1-6}$ alkyl-guanidine, $C_{1-6}$ alkylamino, $C_{1-6}$ alkyl-S—$C_{1-6}$ alkyl, $C_{1-6}$ alkylthiol, $C_{1-6}$ alkyl-hydroxy, $C_{1-6}$ alkyl-amide, $C_{1-6}$ alkyl-phenoxy, $C_{1-6}$ alkyl-carboxy heteroaryl, and heteroaryl-$C_{1-6}$ alkyl, wherein aryl rings can be substituted with from 1 to 3 substituents Z as defined herein, $R^3$ is, independently, H or Cl, with the proviso that at least one $R^3$ is Cl, $R^4$ is, independently, H or —S(O)$_x R^1$, with the proviso that at least one $R^4$ is —S(O)$_x$—$R^1$, Z is selected from the group consisting of $C_{1-8}$ alkyl, $C_{2-6}$ alkenyl, $C_{2-6}$ alkynyl heterocyclyl, aryl, heteroaryl, arylalkoxycarbonyl, carboxy, halo, haloalkyl, —OR', —NR'R", hydroxy, hydroxy-$C_{1-6}$ alkyl, alkoxyalkyl ($C_{2-8}$), alkoxycarbonyl, —CF$_3$, —CN, —NO$_2$, —C$_2$R', —N$_3$, —C(=O)NR'R", —NR'C(=O)R", —C(=O)R', —C(=O)OR', —OC(=O)NR'R", —NR'C(=O)OR", —SO$_2$R', —SO$_2$NR'R", —NR'SO$_2$R", N(R')$_2$, SR', OCOR', N(COR')R', N(COR')COR', and SCOR', Each R' and R" are, independently, H, a $C_{1-6}$ alkyl, $C_{1-6}$ haloalkyl, $C_{1-6}$ alkoxy, $C_{2-6}$ alkenyl, $C_{2-6}$ alkynyl, $C_{3-6}$ cycloalkyl, aryl, heteroaryl, heterocyclyl, alkylaryl, aryl-$C_{1-6}$-alkyl; or if two R' reside on the same nitrogen atom they can come together to form an alkyl ring ($C_{3-6}$) containing none or one heteroatom independently selected from N, O, and S; wherein the R' groups can be substituted with one or more Z substituents as defined above, j is 0-4, and
x is 0-2, or a pharmaceutically acceptable salt or prodrug thereof,
wherein the compound is in the form of the R- or S-configuration at any chiral center.

2. The compounds of claim 1, of the formula:

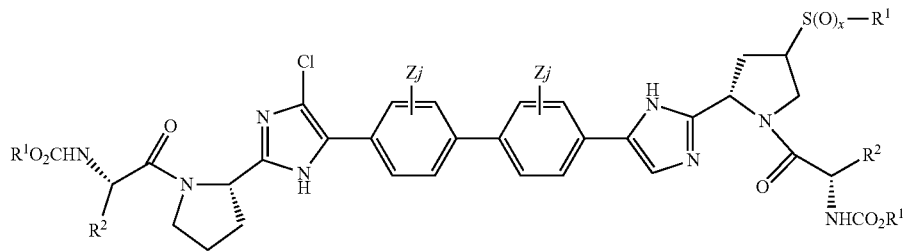

wherein $R^1$, $R^2$, Z, R', R'', j, and x are as defined with respect to Formula (I).

3. The compound of claim 1, wherein one or both of the $R^2$ substituents are phenyl or phenyl substituted with one or more substituents Z as defined herein.

4. The compound of claim 1, wherein one or two of the $R^1$ substituents are —$CH_3$.

5. The compound of claim 1, wherein each $R^1$ is —$CH_3$ and both of the $R^2$ substituents are phenyl or phenyl substituted with one or more substituents Z.

6. A compound having one of the following formulas:

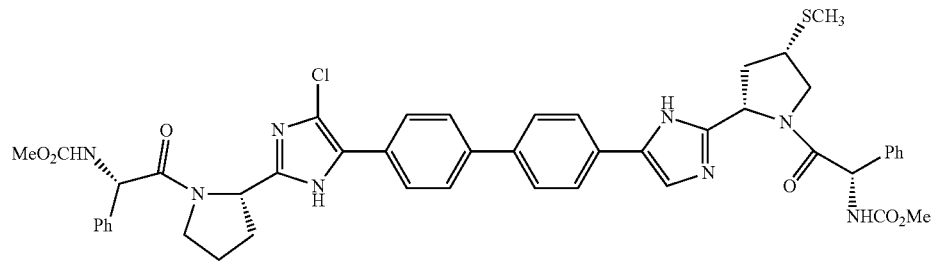

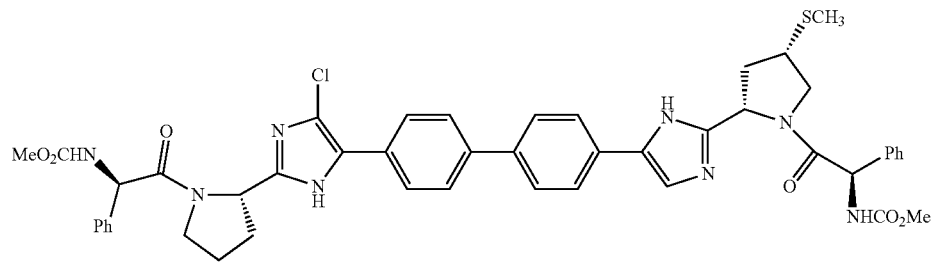

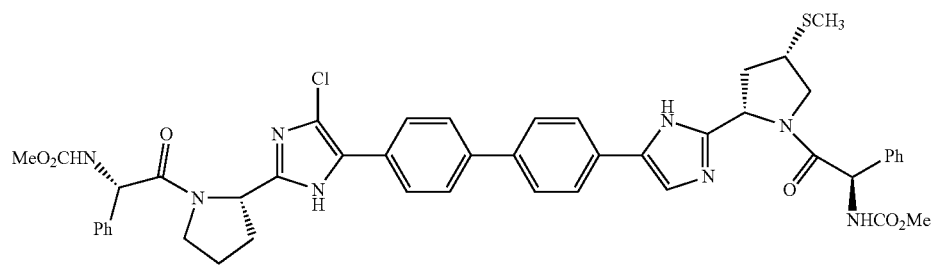

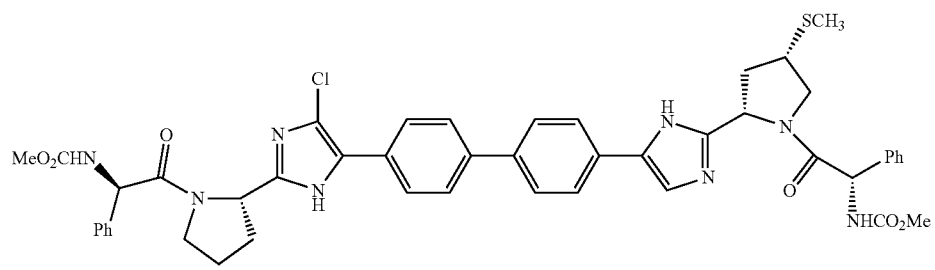

-continued
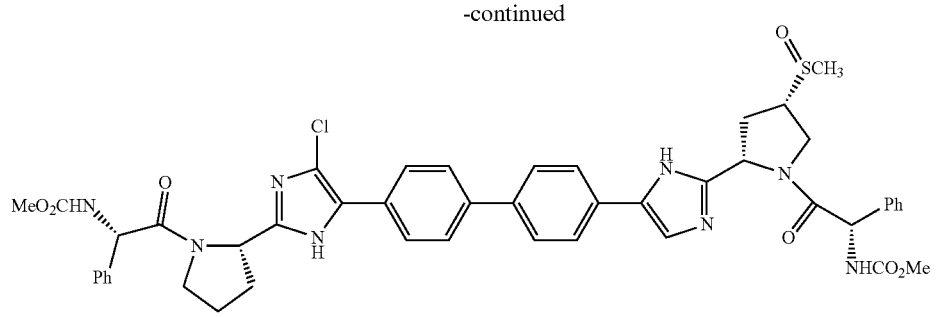
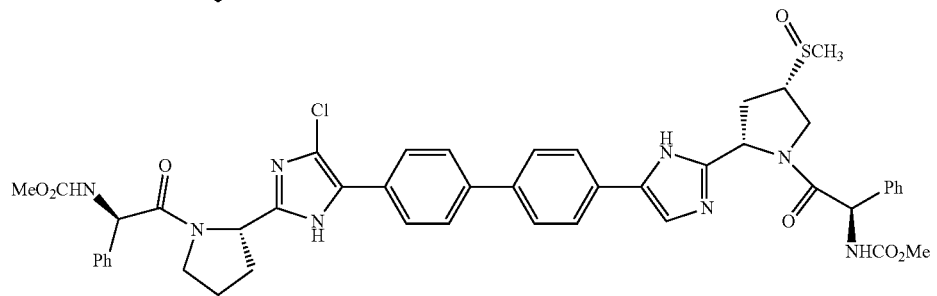
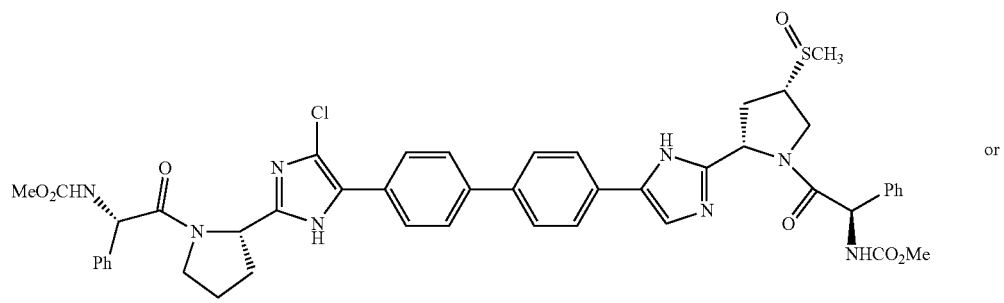 or
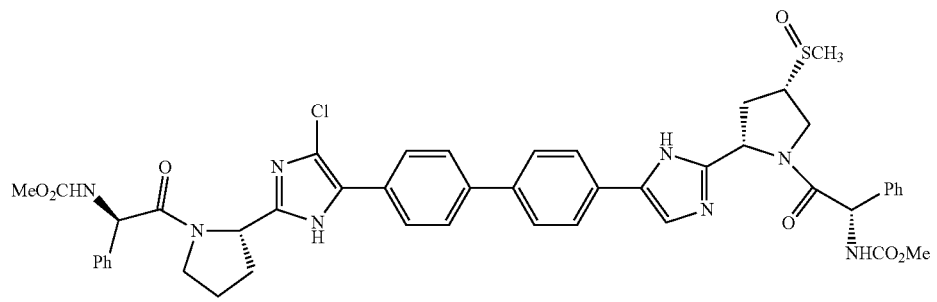
or a pharmaceutically acceptable salt or prodrug thereof.
7. A compound having one of the following formulas:
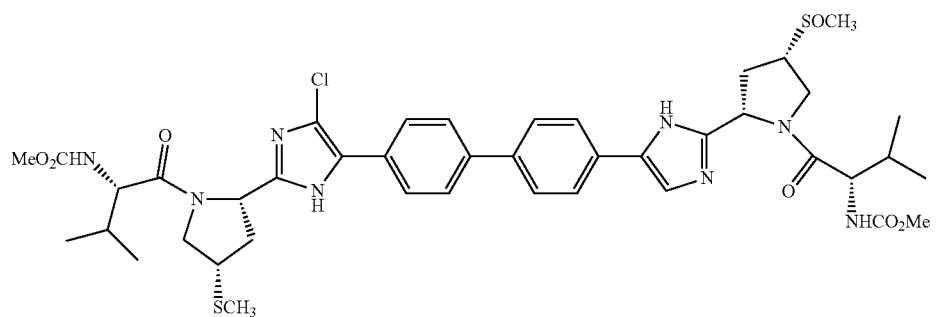

-continued
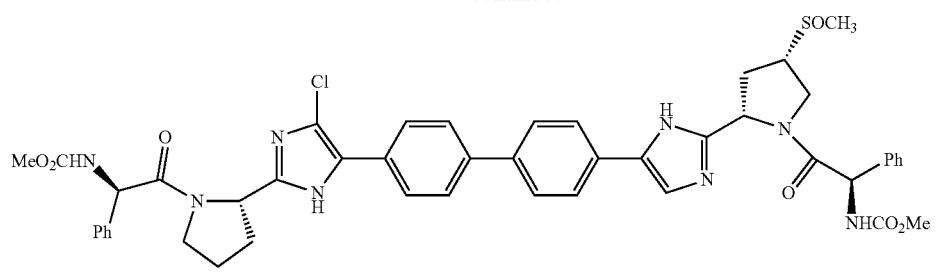
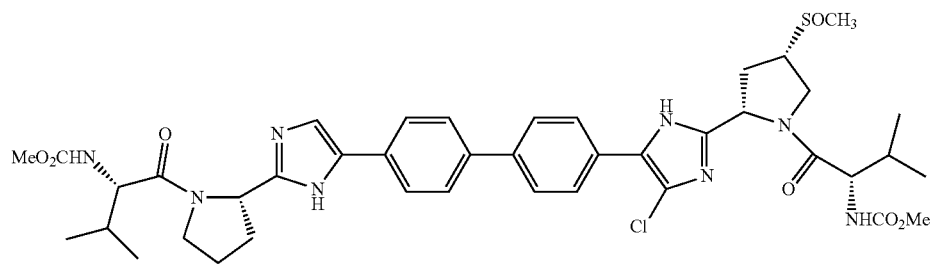
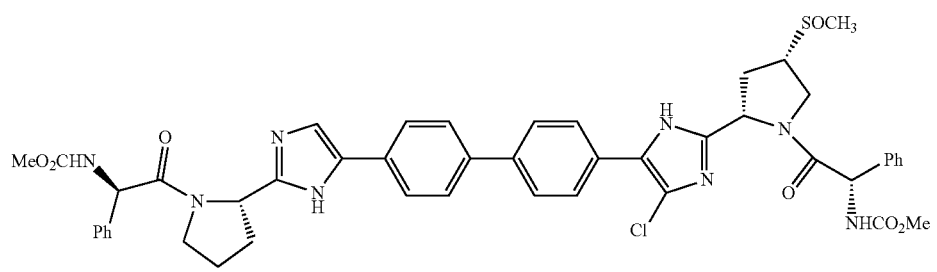
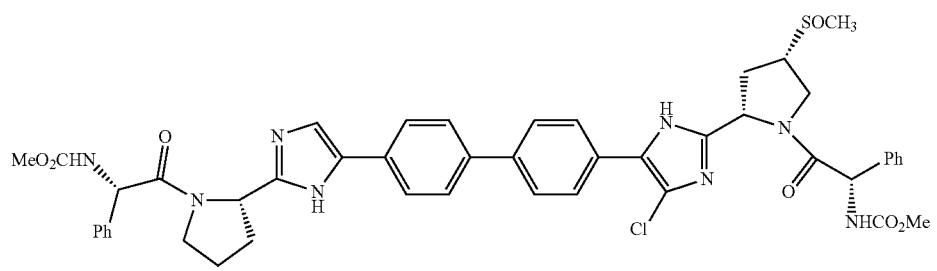
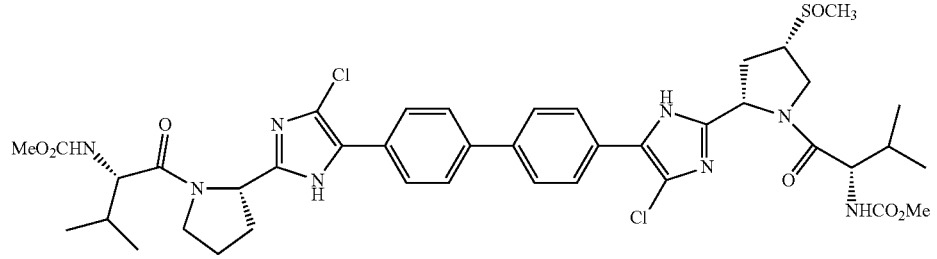
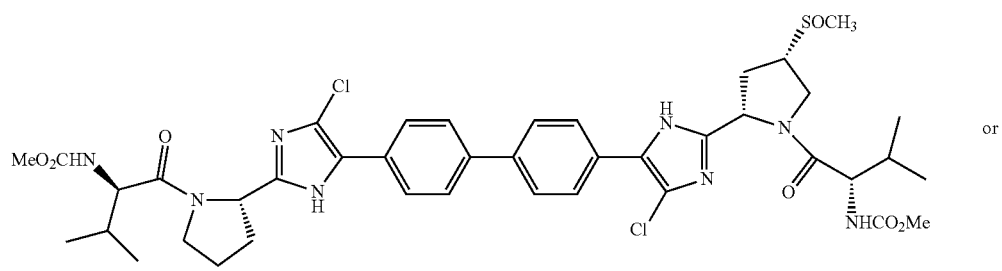 or

-continued

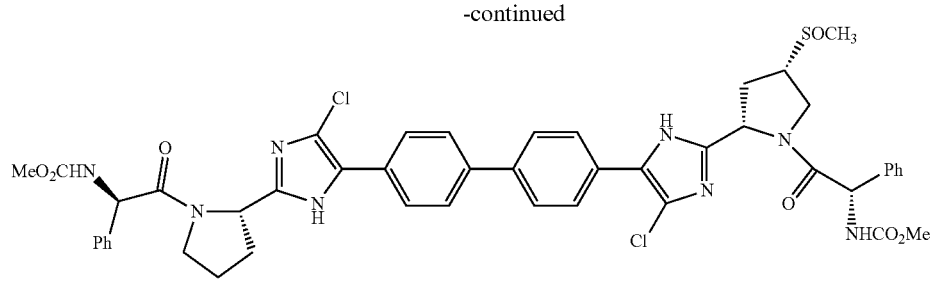

or a pharmaceutically acceptable salt or prodrug thereof.

8. A composition comprising a compound of claim 1, or a pharmaceutically acceptable salt or prodrug thereof, and a pharmaceutically acceptable carrier.

9. The composition of claim 8, further comprising one, two, or three additional compounds having anti-HCV activity.

10. A method for treating a host infected with HCV comprising administering an effective amount of a compound of claim 1 to a patient in need of treatment thereof.

11. The method of claim 10, wherein the compound is administered in combination with one, two, or three other anti-HCV agent(s).

12. The compound of claim 1, wherein one or both of $R^2$ are aryl, wherein each aryl ring can be substituted with from 1 to 3 substituents Z.

13. A compound of Formula (I):

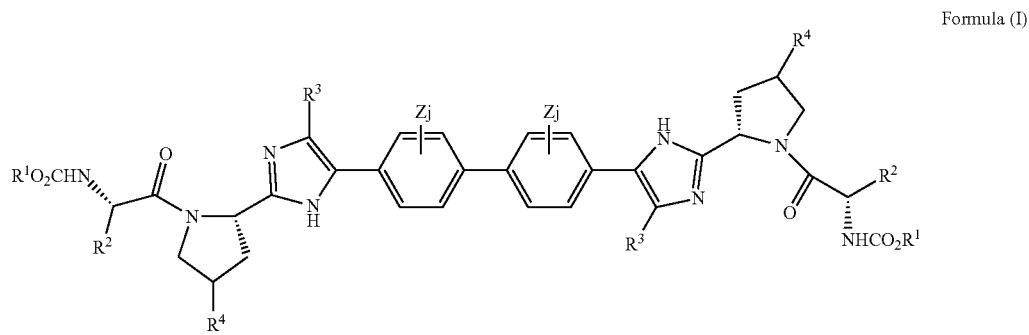

Formula (I)

$R^1$ is, independently, H, $C_{1-6}$ alkyl, aryl-$C_{1-6}$-alkyl, $C_{1-6}$ alkyl-aryl, or aryl, $R^2$ is, independently, H, $C_{1-6}$ alkyl, aryl-$C_{1-6}$-alkyl, $C_{1-6}$ alkyl-aryl, aryl, $C_{1-6}$ alkyl-guanidine, $C_{1-6}$ alkylamino, $C_{1-6}$ alkyl-S—$C_{1-6}$ alkyl, $C_{1-6}$ alkylthiol, $C_{1-6}$ alkyl-hydroxy, $C_{1-6}$ alkyl-amide, $C_{1-6}$ alkyl-phenoxy, $C_{1-6}$ alkyl-carboxy heteroaryl, and heteroaryl-$C_{1-6}$ alkyl, wherein aryl rings can be substituted with from 1 to 3 substituents Z as defined herein, $R^3$ is, independently, H or Cl, with the proviso that at least one $R^3$ is Cl, $R^4$ is, independently, H or —S(O)$R^1$, with the proviso that at least one $R^4$ is —S(O)$R^1$, Z is selected from the group consisting of $C_{1-8}$ alkyl, $C_{2-6}$ alkenyl, $C_{2-6}$ alkynyl heterocyclyl, aryl, heteroaryl, arylalkoxycarbonyl, carboxy, halo, haloalkyl, —OR', —NR'R", hydroxy, hydroxy-$C_{1-6}$ alkyl, alkoxyalkyl ($C_{2-8}$), alkoxycarbonyl, —CF$_3$, —CN, —NO$_2$, —C$_2$R', —N$_3$, —C(=O)NR'R", —NR'C(=O)R", —C(=O)R', —C(=O)OR', —OC(=O)NR'R", —NR'C(=O)OR", —SO$_2$R', —SO$_2$NR'R", —NR'SO$_2$R", N(R')$_2$, SR', OCOR', N(COR')R', N(COR')COR', and SCOR', Each R' and R" are, independently, H, a $C_{1-6}$ alkyl, $C_{1-6}$ haloalkyl, $C_{1-6}$ alkoxy, $C_{2-6}$ alkenyl, $C_{2-6}$ alkynyl, $C_{3-6}$ cycloalkyl, aryl, heteroaryl, heterocyclyl, alkylaryl, aryl-$C_{1-6}$-alkyl; or if two R' reside on the same nitrogen atom they can come together to form an alkyl ring ($C_{3-6}$) containing none or one heteroatom independently selected from N, O, and S; wherein the R' groups can be substituted with one or more Z substituents as defined above, j is 0-4, or a pharmaceutically acceptable salt or prodrug thereof.

* * * * *